(12) United States Patent
Guirguis

(10) Patent No.: US 8,940,527 B2
(45) Date of Patent: *Jan. 27, 2015

(54) INTEGRATED DEVICE FOR ANALYTE TESTING, CONFIRMATION, AND DONOR IDENTITY VERIFICATION

(75) Inventor: Raouf A. Guirguis, Vienna, VA (US)

(73) Assignee: Lamina Equities Corp., Fond du Lac, WI (US)

( * ) Notice: Subject to any disclaimer, the term of this patent is extended or adjusted under 35 U.S.C. 154(b) by 714 days.

This patent is subject to a terminal disclaimer.

(21) Appl. No.: 12/975,471

(22) Filed: Dec. 22, 2010

(65) Prior Publication Data

US 2011/0144535 A1    Jun. 16, 2011

Related U.S. Application Data

(63) Continuation of application No. 12/029,418, filed on Feb. 11, 2008, now Pat. No. 7,879,623, which is a continuation-in-part of application No. 11/394,189, filed on Mar. 31, 2006, now Pat. No. 7,741,103.

(51) Int. Cl.
*C12M 1/34* (2006.01)
*A61B 10/00* (2006.01)
(Continued)

(52) U.S. Cl.
CPC .......... *A61B 10/0051* (2013.01); *G01N 33/558* (2013.01); *G01N 33/94* (2013.01);
(Continued)

(58) Field of Classification Search
CPC .......... G01N 33/5302; G01N 33/5304; G01N 33/558; B01L 2300/04; B01L 2300/041

USPC .......... 422/400, 401, 420, 425, 430; 435/287.2, 287.7, 287.9, 810, 970, 435/973; 436/514, 810

See application file for complete search history.

(56) References Cited

U.S. PATENT DOCUMENTS

| 3,784,358 A | 1/1974 | Drake, Jr. |
| 4,632,901 A | 12/1986 | Valkirs et al. |

(Continued)

FOREIGN PATENT DOCUMENTS

| EP | 0 200 381 | 11/1986 |
| EP | 0 203 238 | 12/1986 |

(Continued)

OTHER PUBLICATIONS

Cone et al. Stability of Cocaine in Saliva Clinical Chemistry vol. 34(7) p. 1508 (1988).

(Continued)

*Primary Examiner* — Chris L Chin
(74) *Attorney, Agent, or Firm* — Hunton & Williams LLP

(57) ABSTRACT

The present invention provides an apparatus for fluid sample collection and analyte testing, including a sample receiving member and at least one membrane test strip, and optionally a sample retention member, fingerprint acquisition pad, and/or fluid collector. It also provides a fluid collection apparatus having an absorbent material, compression element, and closure element, and optionally a lid that allows the apparatus to be used in conjunction with a fluid container. Also provided are methods of collecting, testing, and retaining a fluid sample and verifying the identity of one or more individuals associated with the sample, such as the test subject, test administrator, and/or witnesses.

20 Claims, 18 Drawing Sheets

(51) Int. Cl.
*G01N 33/558* (2006.01)
*G01N 33/94* (2006.01)
*A61B 19/00* (2006.01)

(52) U.S. Cl.
CPC ............. *A61B 10/007* (2013.01); *A61B 19/44* (2013.01); *A61B 2010/0006* (2013.01); *Y10S 435/81* (2013.01); *Y10S 435/97* (2013.01); *Y10S 435/973* (2013.01); *Y10S 436/81* (2013.01)
USPC ........ 435/287.7; 422/400; 422/401; 422/420; 422/425; 422/430; 435/287.2; 435/287.9; 435/810; 435/970; 435/973; 436/514; 436/810

(56) References Cited

U.S. PATENT DOCUMENTS

| | | |
|---|---|---|
| 4,717,656 A | 1/1988 | Swanljung |
| 4,774,192 A | 9/1988 | Terminiello et al. |
| 4,775,636 A | 10/1988 | Moeremans et al. |
| 4,810,630 A | 3/1989 | Craig et al. |
| 4,817,632 A | 4/1989 | Schramm |
| 4,826,759 A | 5/1989 | Guire et al. |
| 4,853,335 A | 8/1989 | Olsen et al. |
| 4,883,764 A | 11/1989 | Kloepfer |
| 4,943,522 A | 7/1990 | Eisinger et al. |
| 4,959,324 A | 9/1990 | Ramel et al. |
| 4,963,325 A | 10/1990 | Lennon et al. |
| 5,006,464 A | 4/1991 | Chu et al. |
| 5,028,535 A | 7/1991 | Buechler et al. |
| 5,071,746 A | 12/1991 | Wilk et al. |
| 5,079,029 A | 1/1992 | Saunders et al. |
| 5,079,172 A | 1/1992 | Hari et al. |
| 5,104,619 A | 4/1992 | De Castro et al. |
| 5,221,627 A | 6/1993 | Grigg et al. |
| 5,244,815 A | 9/1993 | Guirguis |
| 5,260,031 A | 11/1993 | Seymour |
| 5,268,148 A | 12/1993 | Seymour |
| 5,270,167 A | 12/1993 | Francouer |
| 5,283,038 A | 2/1994 | Seymour |
| 5,308,580 A | 5/1994 | Clark |
| 5,342,645 A | 8/1994 | Eisele et al. |
| 5,376,337 A | 12/1994 | Seymour |
| 5,378,492 A | 1/1995 | Mashiko |
| 5,380,492 A | 1/1995 | Seymour |
| 5,393,496 A | 2/1995 | Seymour |
| 5,416,000 A | 5/1995 | Allen et al. |
| 5,441,698 A | 8/1995 | Norell |
| 5,468,648 A | 11/1995 | Chandler |
| 5,494,646 A | 2/1996 | Seymour |
| 5,629,164 A | 5/1997 | Rivers |
| 5,869,345 A | 2/1999 | Chandler |
| 5,876,926 A | 3/1999 | Beecham |
| 5,935,864 A | 8/1999 | Schramm et al. |
| 6,352,863 B1 | 3/2002 | Guirguis |
| 6,365,417 B1 | 4/2002 | Fleming et al. |
| 6,766,817 B2 | 7/2004 | Da Silva |
| 7,060,505 B2 | 6/2006 | Guirguis |
| 7,927,562 B2 | 4/2011 | Wan et al. |
| 2002/0160538 A1 | 10/2002 | Guirguis |
| 2004/0029261 A1 | 2/2004 | Oldfield |
| 2004/0235192 A1 | 11/2004 | Guirguis |
| 2006/0000894 A1 | 1/2006 | Bonalle et al. |
| 2007/0179436 A1 | 8/2007 | Braig et al. |
| 2007/0239069 A1 | 10/2007 | Guirguis |
| 2008/0194041 A1 | 8/2008 | Guirguis |

FOREIGN PATENT DOCUMENTS

| | | |
|---|---|---|
| EP | 0 440 350 | 8/1991 |
| WO | 92/16842 | 10/1992 |
| WO | 93/06486 | 4/1993 |

OTHER PUBLICATIONS

Schramm et al. An Ultrafiltrate of Saliva Collected In Situ as a Biological Sample for Diagnostic Evaluation Clinical Chemistry vol. 37(1) pp. 114-115 (1991).
Wolff et al. Methadone in Saliva Clinical Chemistry vol. 37(7) pp. 1297-1298 (1991).
http://www.craigmedical.com/products.htm visited Jan. 2006.

*Front View*

*Top View*

Back View

Front View

Front View

*Back View*

*Back View*

INTEGRATED DEVICE FOR ANALYTE TESTING, CONFIRMATION, AND DONOR IDENTITY VERIFICATION

CROSS-REFERENCE TO RELATED APPLICATIONS

This application is a continuation of Ser. No. 12/029,418 filed Feb. 11, 2008 (now U.S. Pat. No. 7,879,623, which is a continuation-in-part of Ser. No. 11/394,189 filed Mar. 31, 2006 (now U.S. Pat. No. 7,741,103), and which is hereby incorporated by reference in its entirety.

BACKGROUND OF THE INVENTION

1. Field of the Invention

The present invention relates to substance collection and testing. More particularly, the present invention relates to a device that tests a fluid sample for the presence or absence of at least one analyte, optionally secures the fluid sample for later confirmation, and optionally provides positive identification of an individual associated with the sample. In another aspect, the present invention relates to a device for collecting a fluid sample.

2. Background

Drug and other analyte testing has become ubiquitous in modern society. In homes, doctors' offices, law enforcement, athletics, and the workplace, effective, inexpensive and reliable testing devices have been sought. There is also a growing need for devices to test bodily fluids for substances that may assist in the diagnosis or management of diseases and other medical conditions.

The marketplace has responded and is replete with many devices directed to the testing of blood, urine or saliva. However, these devices may require a series of tests involving the shifting of the fluid sample being tested to different containers and/or the removal of the fluid sample to distant locations. These devices may also require the test administrator to handle the test subject's bodily fluids, incurring a danger of disease exposure.

Once an initial test result has been obtained, further testing of the fluid sample to confirm or refine the initial test result is often required. For a membrane test strip device, the fluid sample may not even be retained once the initial result is obtained, necessitating retention of a separate sample. The need to retain a separate sample incurs the risk that a sample could be lost, mislabeled, or contaminated.

Oftentimes, the chain of custody associated with a test sample imbues the results with doubt, as the fluid sample may become contaminated, misplaced or a different fluid sample may be substituted entirely. In many instances, identification of the test subject associated with the fluid sample is critically dispositive.

There is also a growing need for devices directed to testing for contaminants that may be found in food or water, such as pollutants, allergens, and harmful microbes. In some instances it may be desirable to retain a fluid sample for confirmation testing or further analysis, or to provide positive identification of the test administrator.

These goals are practically impossible to achieve using current devices and methods. Thus, a need exists in the industry to combine the simplicity of current membrane test strip technology with the ability to positively identify the test subject and/or the test administrator, as well as the capability to secure the fluid sample for later confirmation, within a single device.

BRIEF SUMMARY OF THE INVENTION

According to an embodiment, the present invention provides an apparatus comprising: a sample receiving member, to receive a fluid sample; a sample retention member, in fluid communication with the sample receiving member, to retain a portion of the fluid sample; and at least one membrane test strip, in fluid communication with the sample receiving member, to indicate the presence or absence of at least one analyte in the fluid sample.

According to another embodiment, the invention provides an apparatus, comprising: a sample receiving member, having an opening to receive a fluid sample; a fluid collector to collect the fluid sample and convey the fluid sample into the sample receiving member; at least one membrane test strip, in fluid communication with the sample receiving member, to indicate the presence or absence of at least one analyte in the fluid sample, and a fingerprint acquisition pad.

According to a further embodiment, the present invention provides a fluid collector comprising: an absorbent material, to absorb a fluid sample; a compression member operatively associated with the absorbent material; and a closure member, capable of sealing the open end of a sample receiving member when the fluid collector is inserted in the sample receiving member.

According to a still further embodiment, the present invention provides an apparatus comprising: a fluid collector to collect the fluid sample and convey the fluid sample into the sample receiving member, comprising: an absorbent material, to absorb the fluid sample; a compression member operatively associated with the absorbent material; and a closure member, capable of sealing the open end of the sample receiving member when the fluid collector is inserted in the sample receiving member; a sample receiving member, having an opening to receive a fluid sample; a sample retention member, in fluid communication with the sample receiving member, to retain a portion of the fluid sample; at least one membrane test strip, in fluid communication with the sample receiving member, to indicate the presence or absence of at least one analyte in the fluid sample; and a fingerprint acquisition pad.

According to a still further embodiment, the present invention provides a method of testing a fluid sample, comprising: collecting a fluid sample in an absorbent material; conveying the absorbent material into a receiving member of an apparatus; compressing the absorbent material, whereby: the fluid sample is expelled from the absorbent material into channels within the apparatus; the fluid sample encounters at least one membrane test strip within the apparatus that visually indicates the presence or absence of each of one or more analytes; a portion of the fluid sample is retained in a sample retention member of the apparatus; contacting the finger of an individual associated the test with a fingerprint acquisition pad operatively associated with the apparatus, whereby a fingerprint is collected.

BRIEF DESCRIPTION OF THE SEVERAL VIEWS OF THE DRAWINGS

The above and other advantages of this invention will become more apparent by the following description of invention and the accompanying drawings.

DETAILED DESCRIPTION OF THE INVENTION

Analyte Screening

Figure 1:
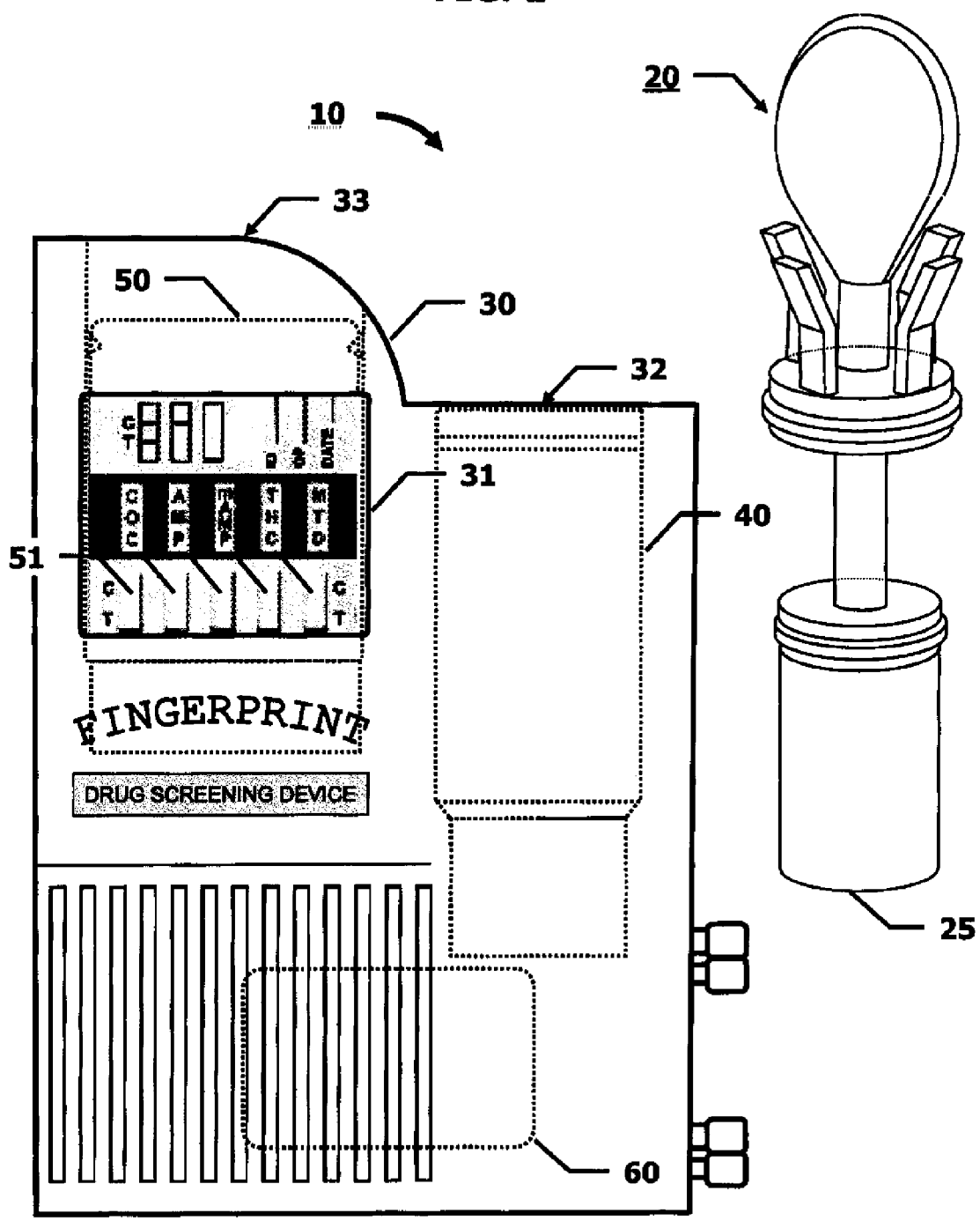
FIG. 1 depicts a front view of a fluid collection and analyte testing device in accordance with an embodiment of the present invention.
Figure 2:
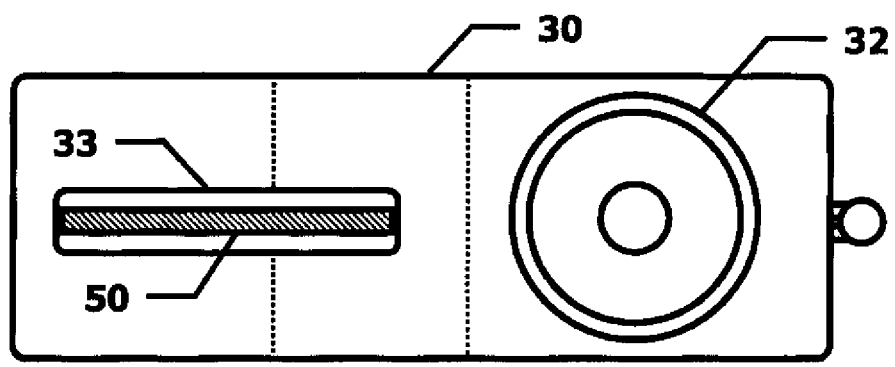
FIG. 2 depicts a top view of a fluid collection and analyte testing device in accordance with an embodiment of the present invention.
Figure 3:
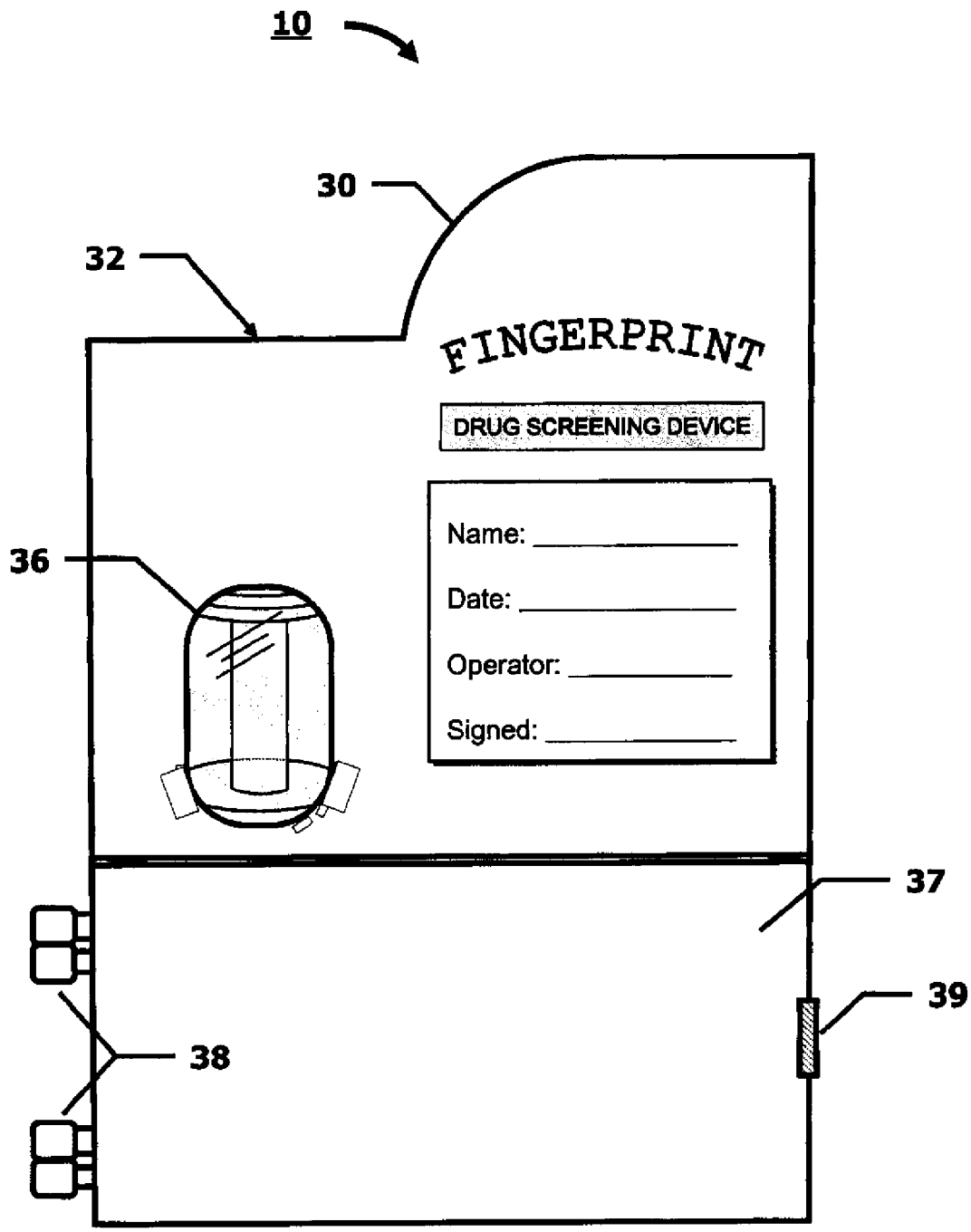
FIG. 3 depicts a back view of a fluid collection and analyte testing device in accordance with an embodiment of the present invention.
Figure 4:
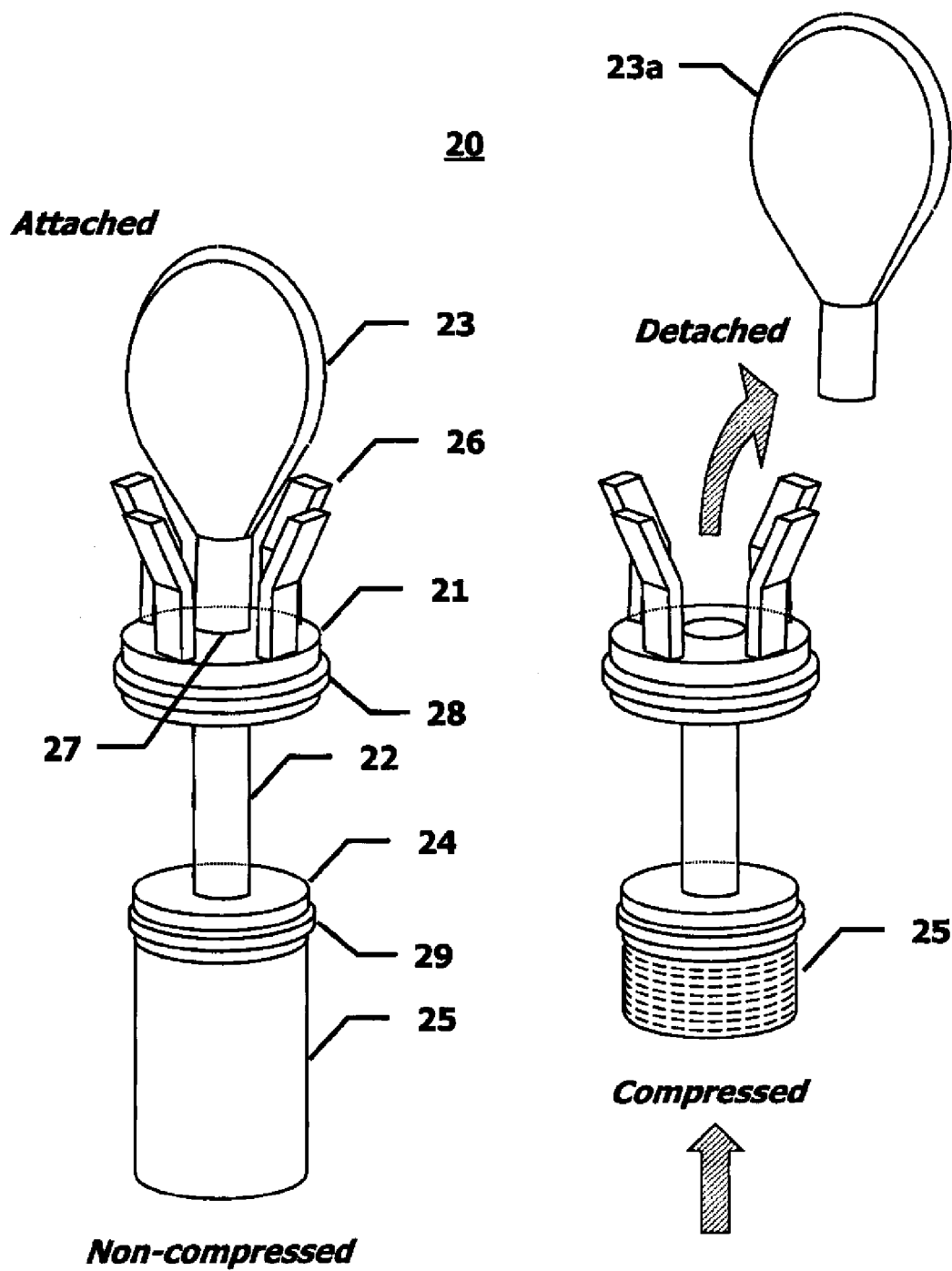
FIG. 4 depicts a two perspective views of a fluid collector in accordance with an embodiment of the present invention.
Figure 5:
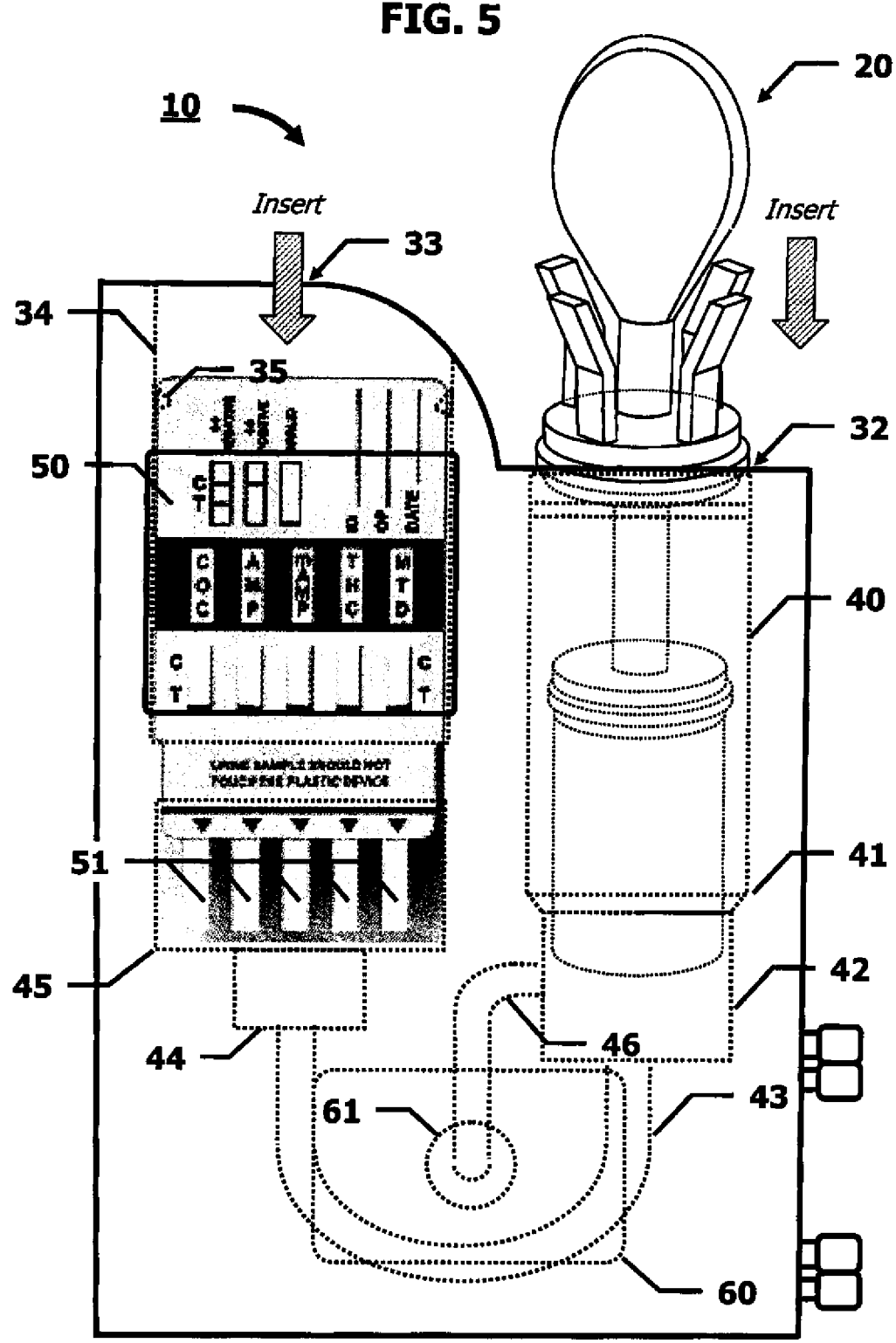
FIG. 5 depicts a front view of a fluid collection and analyte testing device in accordance with an embodiment of the present invention.

An embodiment of the present invention provides an analyte screening device which includes a rapid screening, lateral flow chromatographic immunoassay for the simultaneous, qualitative or quantitative detection of analytes in a fluid sample. For example, without limitation, the fluid sample may be saliva, urine, blood, mucus, water, or fluid extract of a solid or a semi-solid, for example stool or mucus. The fluid sample may also be an environmental sample, for example, without limitation, soil, dust, water, plant matter, insect, animal matter, or a fluid extract of any of the foregoing. The fluid sample may also be a food or beverage, for example, without limitation, a liquid beverage, a liquid-containing food, or a fluid extract of a solid, semi-solid or powdered food or beverage.

An embodiment of the invention includes at least one membrane test strip, in fluid communication with a sample receiving member, able to indicate the presence or absence of at least one analyte above or below a threshold concentration in the fluid sample using a lateral flow chromatographic assay.

In an embodiment of the invention, the lateral flow chromatographic assay is a competitive assay, in which an analyte in the fluid sample competes with a competitor for binding with an anti-analyte antibody. For example, the anti-analyte antibody may be labeled, and the competitor may be immobilized in the test region of the membrane test strip. After the fluid sample reaches the dye region, it encounters the labeled anti-analyte antibody. If the analyte is present in the fluid sample above a predetermined threshold concentration, the analyte will saturate the binding sites of the labeled anti-analyte antibody; otherwise, some or all of the labeled anti-analyte antibody remains free to bind the competitor. As the fluid sample migrates along the membrane test strip by capillary action, it carries the labeled anti-analyte antibody along until it reaches the test region. The test region contains the immobilized competitor, which may be the analyte, fragments of the analyte, epitopes of the analyte, molecular mimics of the analyte, anti-idiotypic antibodies, or any other molecule able to compete with the analyte for binding to the anti-analyte antibody. If the analyte is present above the predetermined threshold concentration, the labeled anti-analyte antibody is saturated and does not bind the immobilized competitor, resulting in no signal in the test region; otherwise, the anti-analyte antibody is unsaturated and can bind to the competitor, resulting in a signal in the test region.

Thus, according to an embodiment of the invention employing a competitive assay, an analyte-negative fluid sample (containing lower than the predetermined concentration of the analyte) will generate a line in the test region due to capture of the labeled anti-analyte antibody, whereas an analyte-positive fluid specimen will not generate a colored line in the test region because the analyte in the fluid sample will saturate the labeled antibody and thus prevent its capture in the test region.

In an embodiment of the invention, the lateral flow chromatographic assay is a sandwich assay, in which the analyte must be present for the labeled anti-analyte antibodies to be captured in the test region. For example, the anti-analyte antibody may be a labeled antibody, and a second anti-analyte antibody may be immobilized in the test region. For example, after the fluid sample reaches the dye region, it encounters the labeled anti-analyte antibody. If the analyte is present in the fluid sample, it will bind at least a fraction of the labeled anti-analyte antibody. As the fluid sample migrates along the membrane test strip by capillary action, it carries the labeled anti-analyte antibody along until it reaches the test region. The test region contains an immobilized anti-analyte antibody, which may be reactive against a different epitope of the analyte than the labeled anti-analyte antibody. If the analyte is present in the fluid sample, it forms a scaffold through which the labeled antibodies are immobilized in the test region. The fraction of the labeled antibodies captured in the test region is thus determined by the concentration of analyte in the fluid sample. If the analyte of interest is present above a predetermined threshold concentration, a sufficient fraction of the labeled antibodies are captured, resulting in a visible signal in the test region; otherwise, an insufficient fraction of the antibodies are captured and no signal is visible in the test region.

Thus, according to an embodiment of the invention employing a sandwich assay, an analyte-positive fluid specimen will generate a colored line in the test region of the membrane test strip due to the capture of the labeled antibody in the test region, whereas an analyte-negative fluid sample will not generate a line in the test region due to failure to capture the labeled antibody.

Embodiments of the invention include a positive control to indicate that the assay has functioned properly and is complete. For example, the dye region may include a labeled control protein, including without limitation a labeled control antibody, and the control region of the membrane test strip may contain an immobilized control agent able to capture the labeled control protein, such as an antibody or a control analyte. The control region may be located distal to each test region on the membrane test strip, such that the fluid sample will encounter each test region before encountering the control region. The reaction of the labeled control protein with the immobilized control agent produces a colored line in the control region, indicating that a proper volume of the fluid sample has been added and membrane wicking has occurred, and the assay has worked properly.

An embodiment of the invention concurrently tests for multiple analytes, for example by employing membrane test strips capable of testing multiple analytes concurrently (for example, by containing multiple anti-analyte antibodies in the dye region and having multiple compatible test region), and/or by employing multiple membrane test strips within the same apparatus. An embodiment of the invention includes both membrane test strips that employ a competitive assay and a sandwich assay, for example on different membrane test strips within the device and/or on the same membrane test strip within the device.

Embodiments of the invention may provide quantitative determination of the concentration of an analyte that is present in the fluid sample. For example, the apparatus may include multiple membrane test strips having varying amounts of an anti-analyte antibody, resulting in varying analyte sensitivity, such that the concentration of the analyte is indicated by which of the membrane test strips show or fail to show a colored line in the test region.

Antibodies

An embodiment of the invention employs antibodies for the detection of analytes. The term "antibody" (Ab) as used herein includes monoclonal antibodies, polyclonal antibodies, multispecific antibodies (for example bispecific antibodies), and antibody fragments, so long as they exhibit the desired activity. The term "monoclonal antibody" as used herein refers to an antibody obtained from a population of substantially homogeneous antibodies, that is, the individual antibodies comprising the population are identical except for possible naturally-occurring mutations that may be present in minor amounts.

The terms "labeled antibody" and "labeled control protein" refer to an antibody or protein that is conjugated directly or indirectly to a label. The label is a detectable compound or composition that may be detectable by itself, including without limitation a dye, colloidal metal (including without limitation colloidal gold), radioisotope, or fluorescent compound, or, in the case of an enzymatic label, may catalyze chemical alteration of a substrate compound or composition which is detectable, or any combination of the foregoing.

Analytes

According to an embodiment of the invention, the apparatus includes a device for testing a fluid sample for the presence of analytes. The present invention contemplates testing for any analyte. Without limitation, analytes that may be tested for include drugs of abuse or their metabolites, analytes indicating the presence of an infectious agent or product of an infectious agent, allergen, pollutant, toxin, contaminant, analyte with diagnostic or medical value, antibody against any of the foregoing, and any combination thereof.

According to an embodiment of the invention, analytes that may be tested for include drugs of abuse and their metabolites, including without limitation 7-acetaminoclonazepam, alkyl nitrites, alpha-hydroxyalprazolam, alprazolam, 2-amino-2'-chloro-5-nitrobenzophenone, 7-aminoclonazepam, 7-aminonitrazepam, amitriptyline, amobarbital, amoxapine, amphetamine, anabolid steroids, androgen, androstadienone, aprobarbital, atropine, barbiturates, benzodiazepines, benzoylecgonine, benzyl piperazine, boldenone undecylenate, 4-bromo-2,5-dimethoxyphenethylamine, bovine growth hormone, butabarbital, butalbital, butriptyline, 4-chlordehydromethyltestosterone, chloroform, clomipramine, clonazepam, clostebol, cocaethylene, cocaine, codeine, codeine-6-glucuronide, cotinine, dehydroepiandrosterone, desipramine, desmethyldiazepam, desoxymethyltestosterone, dexmethylphenidate, dextroamphetamine, dextromethorphan, dextropropoxyphene, dextrorphan, 2,5-diamino-2'-chlorobenzophenone, diamorphine, diazepam, dibenzepin, dihydrotestosterone, dimenhydrinate, 2,5-dimethoxy-4-(n)-propylthiophenethylamine, 2,5-dimethoxy-4-ethylphenethylamine, 2,5-dimethoxy-4-iodophenethylamine, dimethyl ether, dimethyltryptamine, dimethyltryptamine, diphenhydramine hydrochloride, dosulepin hydrochloride, dothiepin hydrochloride, doxepin, drostanolone, ecgonine, ecgonine methyl ester, ephedrine, ergine, estren, 5-estrogen, ethyl-5-(1'-methyl-3'-carboxypropyl)-2-thiobarbituric acid, 5-ethyl-5-(1'-methyl-3'-hydroxybutyl)-2-thiobarbituric acid, ethylestrenol, ethylphenidate, fentanyl, flunitrazepam, fluoxymesterone, furazabol, gamma-hydroxybutyrate, 1-(beta-D-glucopyranosyl) amobarbital, growth hormone, heroine, hexobarbital, human chorionic gonadotropin, human growth hormone, hydrocodone, hydromorphone, (+)-3-hydroxy-N-methylmorphinan, 3-hydroxy clonazepam, 11-hydroxy-tetrahydrocannabinol (11-hydroxy-THC), 3'-hydroxyamobarbital, p-hydroxyamphetamine, p-hydroxynorephedrine, imipramine, iprindole, kava, ketamine, levomethylphenidate, lofepramine, lorazepam, lorazepam-glucuronide, lysergic acid diethylamide, meperidine, mescaline, mestanolone, mesterolone, meta-chlorophenylpiperazine, methadone, methamphetamine, methandrostenolone, methcathinone, 3,4-methylenedioxyamphetamine, methenolone, methenolone enanthate, methylenedioxymethamphetamine (ecstacy), methylphenidate, methylphenobarbital, methyl testosterone, mibolerone, (+)-3-morphinan, morphine, nandrolone, nicotine, nitrazepam, N-methyl-diethanolamine, norbolethone, norcodeine, norethandrolone, norketamine, nortriptyline, opiates, opipramol, opium, oxabolone cipionate, oxandrolone, oxazepam, oxycodone, oxymetholone, oxymorphone, pentobarbital, phencyclidine, phenethylamines, phenobarbital, 4-phenyl-4-(1-piperidinyl)-cyclohexanol, 1-phenyl-1-cyclohexene, phenylacetone, 5-[N-(1-phenylcyclohexyl)]-aminopentanoic acid, 1-(1-phenylcyclohexyl)-4-hydroxypiperidine, piperidine, protriptyline, psilocin, psilocybin, quinbolone, salvinorin A, scopolamine, secobarbital, sodium thiopental, stanozolol, talbutal, temazepam, testosterone, testosterone propionate, tetrahydrocannabinol (THC), THC—COOH, tetrahydrogestrinone, toluene, trenbolone, tricyclic antidepressant, 3-trifluoromethylphenylpiperazine, trimipramine, tryptamines, or any combination thereof. The minimum concentration level at which the presence of any particular drug or metabolite is detected may be determined by various industry minimum standards, such as, for example, the National Institute on Drug Abuse (NIDA), the Substance Abuse & Mental Health Services Administration (SAMHSA), and the World Health Organization (WHO).

According to an embodiment of the invention, analytes that may be tested for include infectious agents or the products of an infectious agent, including without limitation *Acanthamoeba*, aflatoxin, alimentary mycotoxicoses, altertoxin, amoeba, *Anisakis, Ascaris lumbricoides, Bacillus anthracis, Bacillus cereus* or its toxin, bacteria, bovine spongiform encephalopathy prions, *Brucella*, Caliciviridae, *Calymmatobacterium granulomatis, Campylobacter, Campylobacter jejuni, Candida, Candida albicans, Cephalosporium, Chlamydia trachomatis*, chronic wasting disease prions, Citrinin, *Clostridium botulinum* or its toxin, *Clostridium perfringens, Corynebacterium ulcerans, Coxiella bumetii*, Creutzfeldt-Jakob disease prions, *Cryptococcus neoformans, Cryptosporidium, Cryptosporidium parvum*, Cyclopiazonic acid, *Cyclospora cayetanensis*, Cytochalasin, Cytomegalovirus, Diphyllobothrium, *Escherichia Coli*, Ebola, endotoxin, *Entamoeba histolytica*, Enterovirus, Ergopeptine alkaloid, Ergot alkaloid, Ergotamine, *Escherichia coli* O157, *Eustrongylides, Fasciola hepatica*, fatal familial insomnia prions, flatworm, *Francisella tularensis*, Fumitremorgen B, Fumonisin, *Fusarium*, Fusarochromanone, genital warts, Gerstmann-Sträussler-Scheinker syndrome prions, *Giardia, Giardia lamblia, Granuloma inguinale*, H7 enterohemorrhagic, *Haemophilus ducreyi, Helicobacter pylori*, Hepatitis, Hepatitis A, Hepatitis B, Hepatitis C, Hepatitis D, Hepatitis E, Hepatitis E, herpes simplex virus, *Histoplasma capsulatum*, HIV, HIV-1, HIV-2, human papillomavirus, influenza, Kaposi's sarcoma-associated herpesvirus, Kojic acid, kuru prions, *Listeria monocytogenes*, Lolitrem alkaloids, marburg virus, Methicillin-resistant *Staphylococcus aureus* or its toxin, molluscum, Moniliformin, mononucleosis, mycobacteria, *Mycobacterium tuberculosis, Mycoplasma, Mycoplasma hominis*, Mycotoxins, *Myrothecium, Nanophyetus, Neisseria gonorrhoeae*, nematode, Nivalenol, Norovirus, Ochratoxins, Oosporeine, parasites, Patulin, Paxilline, Penitrem A, Phomopsins, *Plasmodium*, Platyhelminthes, *Plesiomonas shigelloides*, Pneumococcus, *Pneumocystis jirovecii*, prions, protozoa, rhinovirus, Rotavirus, *Salmonella, Sarcocystis hominis, Sarcocystis suihominis*, scrapie prions, sexually transmitted disease, *Shigella, Shigella*, Sporidesmin A, *Stachybotrys, Staphylococcus aureus* or its toxin, *Sterigmatocystin, Streptococcus, Streptococcus pneumoniae, Streptococcus pyogenes, Taenia saginata, Taenia solium*, tapeworm, *Tenia solium*, Tinea, *Toxoplasma gondii, Tremorgenic mycotoxins, Treponema pallidum, Trichinella spiralis, Trichoderma, Trichomonas vaginalis*, Trichothecene, *Trichuris trichiura, Trypanosoma cruzi, Ureaplasma urealyticum*, Verrucosidin, Verruculogen, *Vibrio cholerae* non-O1, *Vibrio cholerae* O1, *Vibrio parahaemolyticus, Vibrio vulnificus*, viruses, yeast infections, *Yersinia enterocolitica, Yersinia pseudotuberculosis*, Zearalenols, Zearalenone, antibodies against any of the foregoing, or any combination thereof.

According to an embodiment of the invention, the analytes to be tested for include allergens, including without limitation aesculus, alder, almonds, animal products, *artemisia vulgaris*, beans, bee sting venom, birch, calyx, cat dander, celeriac, celery, chenopodium album, cockroach, corn, dander, dog dander, drugs, dust mite excretion, egg albumen, eggs, Fel d 1 protein, fruit, fur, grass, hazel, hornbeam, Insect stings, latex, legumes, local anaesthetics, maize, metal, milk, mold spores, mosquito saliva, mouse dander, nettle, olea, peanuts, peas, pecans, penicillin, Plant pollens, plantago, platanus, poplar, pumpkin, ragweed, rat dander, ryegrass, salicylates, seafood, sesame, sorrel, soy, soybeans, sulfonamides, tilia, timothy-grass, tree nuts, trees, wasp sting venom, weeds, wheat, willow, antibodies against any of the foregoing, or any combination thereof.

According to an embodiment of the invention, the analytes to be tested for include pollutants, toxins, and contaminants, including without limitation 1,2-Dibromoethane, acrylamide, aldehydes, arsenic, artificial growth hormone, asbestos, benzene, benzopyrene, carcinogens, dichloro-diphenyl-trichloroethane, formaldehyde, kepone, lead, mercury, methylmercury, nitrosamines, N-nitroso-N-methylurea, organochlorine insecticides, pesticides, polychlorinated biphenyls, polychlorinated dibenzofurans, polychlorinated dibenzo-p-dioxins, recombinant bovine growth hormone, recombinant bovine somatotropin, toluene, vinyl chloride, antibodies against any of the foregoing, or any combination thereof.

According to an embodiment of the invention, the analytes to be tested for include analytes with diagnostic or medical value, including without limitation acid phosphatase, active-B12, AFP, Alanine Aminotransferase, Alanine Aminotransferase, Albumin, Albumin BCG, Albumin BCP, Alkaline Phosphatase, Alpha-1 Antitrypsin, Alpha-1 Glycoprotein, Amikacin, Ammonia, Amylase, Anti-CCP, Anti-Tg, Anti-TPO, Apolipoprotein A1, Apolipoprotein B, ASO, Asparate Aminotransferase, Aspartate Aminotransferase, B12, Beta2 Microglobulin, Beta2 Microglobulin, BNP, CA 125, CA 125 II, CA 15-3, CA 19-9 XR, Calcium, Carbamazepine, Carbon Dioxide, CEA, Ceruloplasmin, Cholesterol, CK-MB, Complement C3, Complement C4, Cortisol, C-Peptide, C-Reactive Protein, Creatine Kinase, Creatinine, CRP Vario, Cyclosporine, Cyclosporine and Metabolite—Whole Blood, Cyclosporine Monoclonal—Whole Blood, D-Dimer, DHEA-S, Digitoxin, Digoxin, Digoxin II, Digoxin III, Direct Bilirubin, Direct LDL, Estradiol, Ferritin, FLM II, Folate, Free Carbamazepine, Free Phenyloin, Free PSA, Free T3, Free T4, Free Valproic acid, FSH, Gamma-Glutamyl Transferase, Gentamicin, Glucose, Glycated Hemoglobin, Haptoglobin, hCG, Hemoglobin, Homocysteine, ICT CI-, IGFBP-1, Immunoglobulin, Immunoglobulin A, Immunoglobulin E, Immunoglobulin G, Immunoglobulin M, Insulin, Intact PTH, Iron, K+, Kappa Light Chain, Lactate Dehydrogenase, Lactic acid, Lambda Light Chain, LH, Lidocaine, Lipase, Lithium, Lp, Magnesium, metabolites, Methotrexate II, Microalbumin, MPO, Myoglobin, Na+, N-Acetyl-procainamide, Neonatal Bilirubin, NGAL, P-Amylase, Pepsinogen I, Pepsinogen II, Phenobarbital, Phenyloin, Phosphorus, Prealbumin, Procainamide, Progesterone, Prolactin, Quinidine, Rheumatoid Factor, SHBG, Sirolimus, STAT CK-MB, T4, Tacrolimus, Tacrolimus II, Testosterone, Tg, Theophylline, Theophylline II, TIBC, TIMP-1, Tobramycin, Total Bilirubin, Total Estriol, Total Protein, Total PSA, Total T3, Total T4, Transferrin, Triglycerides, Troponin-I, Troponin-I ADV, TSH, T-Uptake, UIBC, Ultra HDL, Urea Nitrogen, Uric Acid, Urine/CSF Protein, Valproic Acid, Vancomycin, Vancomycin II, Vitamin D, antibodies against any of the foregoing, or any combination thereof.

Receiving Member

According to an embodiment of the invention, the apparatus includes a receiving member, having an opening to receive a fluid sample. For example, the receiving member may be dimensioned to receive a fluid collector. In an embodiment of the invention, the receiving member may be in fluid communication with other components of the apparatus, for example at least one membrane test strip, sample retention member, and/or an immunoassay-based fingerprint acquisition pad, through channels, for example tubes, piping, channels molded or carved into the apparatus, or any other suitable structure, made of any suitable material, for example plastic, ceramic, metal, glass, wood, rubber, polymer, fiber-reinforced polymer, or any combination thereof.

According to an embodiment of the invention, the channel or channels providing fluid communication between the components may have differing flow resistance, for example having channels, channel segments, or openings, that are narrower, wider, longer, or shorter than others, and/or having fluid paths with varying amounts of vertical rise or drop, such that the fluid channels within the device have varying degrees of flow resistance. For example, the channel that provides the fluid communication of the sample receiving member with the at least one membrane test strip may have greater flow resistance than the at least one channel that provides the fluid communication of the sample receiving member with the sample retention member, to ensure that a portion of the fluid sample is collected in the sample retention member.

In an embodiment of the invention, a single channel having multiple openings may connect the receiving member to each of the components of the apparatus with which it is in fluid communication, for example the at least one membrane test strip, sample retention member, and/or immunoassay-based fingerprint acquisition pad.

An embodiment of the invention may accommodate fluids of varying viscosity, for example water, saliva, urine, and blood. Generally this is accomplished by varying the diameter of the channel or channels that provide the fluid communication of the sample receiving member with the other components of the apparatus, for example providing a wider channel diameter to accommodate a more viscous fluid.

In an embodiment of the invention, a channel dimensioned to be compatible with a fluid having the viscosity of water provides the fluid communication of the sample receiving member with the at least one membrane test strip and at least one channel dimensioned to be compatible with a fluid having the viscosity of water provides the fluid communication of the sample receiving member with the sample retention member.

In an embodiment of the invention, a channel dimensioned to be compatible with a fluid having the viscosity of urine provides the fluid communication of the sample receiving member with the at least one membrane test strip and at least one channel dimensioned to be compatible with a fluid having the viscosity of urine provides the fluid communication of the sample receiving member with the sample retention member.

In an embodiment of the invention, a channel dimensioned to be compatible with a fluid having the viscosity of saliva provides the fluid communication of the sample receiving member with the at least one membrane test strip and at least one channel dimensioned to be compatible with a fluid having the viscosity of saliva provides the fluid communication of the sample receiving member with the sample retention member.

In an embodiment of the invention, a channel dimensioned to be compatible with a fluid having the viscosity of blood provides the fluid communication of the sample receiving member with the at least one membrane test strip and at least one channel dimensioned to be compatible with a fluid having the viscosity of blood provides the fluid communication of the sample receiving member with the sample retention member.

In an embodiment of the invention, a channel dimensioned to be compatible with a fluid having the viscosity of mucus provides the fluid communication of the sample receiving member with the at least one membrane test strip and at least one channel dimensioned to be compatible with a fluid having the viscosity of mucus provides the fluid communication of the sample receiving member with the sample retention member.

In an embodiment of the invention, the receiving member may have an inner surface, for example a lower surface, that an absorbent material, such as an absorbent material present in a fluid collector, may be compressed against, thereby expelling the fluid sample from the absorbent material. For example, the absorbent material may be compressed directly between a compression member present on the fluid collector and the lower surface of the receiving member, or the receiving member may provide structural support to facilitate compression of the absorbent material between a compression member and the housing that at least partially surrounds the absorbent material.

Sample Retention Member

According to an embodiment of the invention, the apparatus includes a sample retention member. The sample retention member may be used to securely contain a portion of the fluid sample. The retained portion of the fluid sample may be used for further testing, for example for confirmation of a test result obtained using a membrane test strip, or to test for the presence or absence of other analytes in the fluid sample. The retained portion of the fluid sample may also be used for confirmation of the test subject's identity through analysis of a distinguishing feature thereof, including without limitation DNA.

According to an embodiment of the invention, the sample retention member includes an absorbent material, for example a pad or sponge, or made of woven or non-woven fibrous or fabric-like material, for example cellulose or a cellulose derivative, cotton, hydrophilic foam, wood pulp, polyvinyl alcohol fibers, or any combination thereof. The sample retention member may include an absorbent material that is part of the sample collection apparatus. The absorbent material may be surrounded by a barrier, such as a liquid-impermeable material, including without limitation plastic, ceramic, metal, glass, wood, rubber, polymer, fiber-reinforced polymer, or any combination thereof, to prevent the retained sample from leaking or evaporating. In an embodiment of the invention, the absorbent material may be removably attached to the apparatus to facilitate retrieval of the retained fluid sample. In an embodiment of the invention, the absorbent material may be accessed using a needle, for example by piercing a barrier surrounding the absorbent material. The retained sample may then be removed, for example, into a syringe attached to a needle, by means of withdrawal of the syringe to create suction.

According to an embodiment of the invention, the sample retention member includes a storage container defining a volume for storage of the fluid sample. In an embodiment of the invention, the storage container may be accessed using a needle to pierce the wall of the storage container. For example, the storage container may include a pierceable member, such as a region of decreased wall thickness, and/or made of a soft, pierceable, or breakable material, including without limitation plastic, ceramic, metal, glass, metal foil, wood, rubber, polymer, fiber-reinforced polymer, or any combination thereof, that may be pierced. The retained sample may then be removed, for example, into a syringe attached to a needle, by means of withdrawal of the syringe to create suction. In an embodiment of the invention, the storage container may be removably attached to the apparatus, for example through a line of weakness that may allow the storage container to be broken free from the apparatus.

According to an embodiment of the invention, the sample retention member contains substances that facilitate a further use of the sample, including without limitation preservatives or stabilizers able to preserve sample integrity, for example substances able to inhibit microbial growth, kill microbes, prevent sample leakage, prevent sample evaporation, inhibit chemical or enzymatic degradation of substances in the sample, support survival of cells or other microbes in the sample, or any combination thereof.

According to an embodiment of the invention, the sample retention member may be bonded to a fingerprint acquisition pad. For example, such a bond may provide a safeguard against dissociation of the retained sample from the fingerprint.

The retained fluid sample may be used for further confirmation testing, including without limitation gas chromatography, liquid chromatography, mass spectrometry, liquid or gas chromatography with tandem mass spectrometry, polymerase chain reaction, DNA sequencing, Enzyme-Linked ImmunoSorbent Assay, Western Blotting, culturing for growth, or any combination thereof, using the retained fluid sample.

Fluid Collector

An embodiment of the apparatus comprises a fluid collector for collecting a fluid sample. The present invention contemplates collecting a sample from a specific subject, such as a human subject, or testing environmental samples, such as testing air, water, soil, or some other substance, or a food or beverage, or a liquid extract of any of the foregoing for example, without limitation. The fluid collector is operative associated with the apparatus. The fluid collector may be removably associated with the apparatus, affixed to the apparatus, or comprise multiple units of which one or more is affixed or removably associated with the apparatus.

In an embodiment of the invention, the fluid collector includes an absorbent material capable of absorbing a desired quantity of a fluid sample. The absorbent material may be made of any suitable material known to a person in the art, for example, without limitation, a pad or sponge, or woven or non-woven fibrous or fabric-like material, including without limitation cellulose or a cellulose derivative, cotton, hydrophilic foam, wood pulp, polyvinyl alcohol fibers, or any combination thereof. In an embodiment of the invention, the fluid collector includes a compression member, able to compress the absorbent material, that may be used to expel air from the absorbent material prior to collection of the fluid sample and/or to encourage the fluid sample to flow into the absorbent material by creating suction as the compressed absorbent material returns to the uncompressed state. A compression member may also be used, for example, to compress the absorbent material and expel a fluid sample contained therein.

A sufficiency indicator on the collector is contemplated. For example without limitation, a color indicator may either appear or disappear when a sufficient sample has been collected, for example when a sufficient volume has been absorbed to reach the location in the absorbent material where the sufficiency indicator is disposed. According to an embodiment of the invention, the sufficiency indicator may be operatively associated with the absorbent material and may protected from direct contact with the source of the fluid sample by a barrier, such as a transparent barrier, for example plastic or glass, such that the fluid sample will only reach the sufficiency indicator by passing into the absorbent material.

The sufficiency indicator color may be in the shape of a word or symbol that appears or disappears when a sufficient sample has been collected. For example, the sufficiency indicator may a diffusible dye, wherein dilution of the dye by the fluid sample causes a color to disappear, indicating that a sample of sufficient volume has been collected. In an embodiment of the invention, a combination of a non-diffusible and diffusible dye may be used together, such that the non-diffusible dye remains and provides an informative message when the diffusible dye disappears, for example the diffusible dye may form the letters "in" in the word "insufficient" such that the non-diffusible dye remains and forms the word "sufficient" when a sufficient sample has been collected.

The sufficiency indicator may be a pH-sensitive substance that changes color when the sample is encountered. For example, multiple pH sensitive indicators responding to different pH values may be present, such that a color change is observed whether the sample is acidic, basic, or neutral. According to an embodiment of the invention, a pH-changing substance, such as an acid or base, may be disposed within the absorbent material, such that the sample will be of the correct pH to elicit the desired color change in the sufficiency indicator.

A closure member may be used. The closure member is capable of sealing the open end of a sample receiving member when the fluid collector is inserted into the open end of a sample receiving member. For example, the closure member may be dimensioned to fit closely in the opening in the open end of the receiving member, and the closure member or the open end of the receiving member may include a compressible material, including without limitation natural rubber such as vulcanized rubber, synthetic rubber such as neoprene or nitrile rubber, plastic, ceramic, or any combination thereof, disposed at the interface between the closure member and the opening in the open end of the sample receiving member, capable of creating a seal, such as an airtight or a watertight seal, when the sample receiving member receives the fluid collector.

After the fluid collector has been inserted into the sample receiving member, a device for securing the fluid collector within the sample receiving member is contemplated. The means for securing may prevent removal of the fluid collector from the sample receiving member after it has been inserted therein. The means for securing the fluid collector within the sample receiving member may include at least one projection extending from the fluid collector that cooperates with the at least one projection located on the inner surface of the sample receiving member, where such projections may include for example at least one locking tab and/or at least one annular ring. According to an embodiment of the invention, a closure member on the fluid collector may form a sufficiently secure closure as to constitute means for securing the fluid collector within the sample receiving member.

The sample receiving member may also include a tamper-evident seal, such that attempting to tamper with the contents of the apparatus will result in a visual indicator, for example by tears or breakage visible in an imprinted seal, for example tape or adhesive-backed foil having characters, symbols or a signature on a surface. Such a tamper-evident seal may be placed on the apparatus before its use, to create a visual confirmation that the contents of the apparatus have not been altered via the open end of the receiving member prior to testing, or after its use, to create a visual confirmation that the contents of the apparatus have not been altered via the open end of the receiving member subsequent to testing. According to an embodiment of the invention, the means for securing the fluid collector within the sample receiving member may constitute a tamper evident seal, in that attempted removal of the fluid collector from the sample receiving member after it has been inserted therein may result in visible damage to the apparatus.

According to an embodiment of the invention, the fluid collector includes a handle, for example made of wood, plastic, ceramic, or metal, and disposed, for example, at the end distal to the absorbent material. The handle may be removably attached, for example through an interference fit, adhesive, glue, or epoxy, that breaks or separates when the handle is twisted and/or pulled, or by a structure that allows the handle to be broken away, for example, a line of weakness.

The fluid collector may include a housing that at least partially surrounds the absorbent material. The housing may have multiple openings to allow the fluid sample to be absorbed by and expressed from the absorbent material. The openings in the housing may contain filtration members able to strain particulates from the fluid sample, resulting in reduction of the number of particulates that enter the absorbent material. The fluid collector may include a compression member able to compress the absorbent material against the housing. For example, the housing may be slidably coupled to a compression member with the absorbent material disposed between the compression member and an inner surface of the housing, such that the absorbent material may be compressed by movement of the compression member towards an inner surface of the housing. An embodiment of the invention includes means for securing the absorbent material in the compressed state, including without limitation cooperating threads, projections, and/or grooves operatively associated with the compression member and the housing. The absorbent material may be released from the compressed state before, concurrently with, or after encounter with the fluid sample, facilitating entry of the fluid sample into the absorbent material as the absorbent material returns to the relaxed state, creating suction. For example, the absorbent material may be operatively associated with a spring, such that compression of the absorbent material results in compression of the spring, and when compression is released the spring assists return of the absorbent material to the uncompressed state.

In an embodiment of the invention, the fluid collector is operatively associated with the lid of a fluid container including without limitation a urine cup. For example, the absorbent material may be disposed on the inner side of the lid, such that attachment of the lid to the fluid container results in contact between the absorbent material and a fluid sample. In certain embodiments of the invention, a portion of the fluid collector including the lid may be removably associated with a portion of the fluid collector including the absorbent material, allowing the absorbent material to be separated from the lid. The operative association of the fluid collector with the lid may include means for arresting the rotation of part of the fluid collector relative to the lid, including without limitation cooperating projections present on one member and grooves or slots present on the other member, for example to facilitate release of means by which the absorbent material is fixed in the compressed state.

Saliva Producing Substances

Use of a saliva producing substance is contemplated by the present invention. Saliva producing substances elicit or increase saliva production in the test subject. For example, without limitation, the saliva producing substance may sugars, salts, acids, or any combination thereof. In an embodiment of the invention, the saliva producing substance may be associated with a fluid collector, for example located on or in the absorbent material or the housing. In an embodiment of the invention, the saliva producing substance may be separated from the fluid collector, for example in the form of a gum, candy, or powder, for administration to the test subject before, during or after the fluid collector is inserted into the test subject's mouth.

For example, without limitation, the sugar may be a monosaccharide, a disaccharide, a trisaccharide, an oligosaccharide, a polysaccharide, acarbose, allose, altrose, amylose, arabinose, cellobiose, cyclodextrin, alpha-cyclodextrin, beta-cyclodextrin, gamma-cyclodextrin, deoxyglucose, dextrin, dihydroxyacetone, erythrose, erythrulose, ficoll, fructo-oligosaccharides, fructose, galacto-oligosaccharides, galactose, gentiobiose, glucosamine, glucose, glyceraldehyde, glycogen, gulose, idose, inositol, inulin, isomaltose, lactose, lyxose, maltose, maltosyl-cyclodextrin, malt-triose, mannan-oligosaccharides, mannoheptulose, mannose, melezitose, monnitol, psicose, raffinose, ribitol, ribose, ribulose, sedoheptulose, sorbitol, sorbose, sucrose, tagatose, talose, threose, trehalose, xylose, xylulose, or any combination thereof.

For example, without limitation, the salt may an inorganic salt, organic salt, acid salt, alkali salt, neutral salt, or amino acid salt, or any combination thereof. The salt may include a cation and an anion, for example without limitation thereto, the cation may be aluminium, ammonium, barium, beryllium, calcium, cesium, chromium(II), chromium(III), chromium (VI), cobalt(II), cobalt(III), copper(I), copper(II), copper (III), gallium, helium, hydrogen, hydronium, iron(II), iron (III), lead(II), lead(IV), lithium, magnesium, manganese(II), manganese(III), manganese(IV), manganese(VII), nickel (II), nickel(III), nitronium, potassium, pyridinium, silver, sodium, strontium, tin(II), tin(IV), zinc, or any combination thereof, and an anion may be acetate, amide, tartrate, borate, bromate, bromide, carbonate, chlorate, chloride, chlorite, chromate, citrate, cyanate, dichromate, dihydrogen phosphate, fluoride, formate, glutamate, hydride, hydrogen carbonate, hydrogen oxalate, hydrogen phosphate, hydrogen sulfate, hydrogen sulfite, hydroxide, hypobromite, hypochlorite, iodate, iodide, nitrate, nitride, nitrite, oxalate, oxide, perchlorate, permanganate, peroxide, phosphate, phosphide, phosphite, pyrophosphate, sulfate, sulfide, sulfite, telluride, thiocyanate, thiosulfate, or any combination thereof. For example, according to an embodiment of the invention, the salt may be sodium chloride or potassium chloride.

The acid may be any suitable acid known to a person skilled in the art, for example acetic acid, acrylic acid, adipic acid, alginic acid, alkanesulfonic acid, amino acid, ascorbic acid, benzoic acid, boric acid, butyric acid, carbonic acid, carboxylic acid, citric acid, fattys acid, folic acid, formic acid, fumaric acid, gluconic acid, hydriodic acid, hydrobromic acid, hydrochloric acid, hydroquinosulfonic acid, isoascorbic acid, lactic acid, maleic acid, malic acid, malonic acid, methanesulfonic acid, nitric acid, oxalic acid, p-toluenesulfonic acid, para-bromophenylsulfonic acid, phosphoric acid, propionic acid, salicylic acid, stearic acid, succinic acid, sulfuric acid, tannic acid, tartaric acid, thioglycolic acid, toluenesulfonic acid, uric acid, or any combination thereof.

Fingerprint Identification

An embodiments of the present invention includes a fingerprint pad to provide identification of an individual associated with the test, such as the test subject, test administrator, and/or one or more witnesses. The fingerprint pad may employ any suitable fingerprinting methodology, for example, without limitation, ink-based, immunoassay-based, electronic, semi-inkless, or inkless. In an embodiment of the invention, the fingerprint pad may be able to collect multiple fingerprints, for example having multiple fingerprint pads, having one fingerprint pad of sufficient size to accommodate multiple fingerprints, or having an electronic fingerprint pad.

The fingerprint pad may be an ink-based fingerprint pad. An embodiment of the invention includes a dispenser able to dispense an ink that can elicit a signal in the ink-based fingerprint pad. The fingerprint pad may also be inkless or semi-inkless, for example requiring no ink or compatible with an activator that appears transparent on the subject's skin, is readily cleaned off of the subject's skin, or readily disappears, for example when the subject's hands are rubbed together. According to an embodiment of the invention, the inkless fingerprint pad may be immunoassay-based, for example as described within U.S. Pat. No. 6,352,863 to Raouf A. Guirguis, issued Mar. 5, 2002 (the "'863 patent"), and U.S. Pat. No. 5,244,815 to Raouf A. Guirguis, issued Sep. 14, 1993 (the "'815 patent"), which are incorporated herein by reference in their entirety. The immunoassay-based fingerprint pad may or may not be in fluid communication with a sample receiving member. Other embodiments of the invention may incorporate various features of the embodiments disclosed within the '863 and '815 patents. In embodiment of the invention having an inkless or semi-inkless fingerprint pad that requires an activator to elicit a signal, the apparatus may also include a dispenser to dispense the activator. According to an embodiment of the invention, the fingerprint pad may have a surface, such as an absorbent or adhesive surface, able to gather sweat, oils, and/or skin cells when a finger is pressed against it, that may require further processing to permit clear visualization of the fingerprint.

According to an embodiment of the invention, an inkless fingerprint pad may be an electronic fingerprint pad, including without limitation an optical scan fingerprint reader or a solid-state fingerprint reader. An embodiment of the invention includes a memory element, including without limitation volatile or non-volatile memory, for example a hard disk, floppy disk, magnetic tape, optical disk, flash memory, holographic memory, EEPROM, RAM, DRAM, SDRAM, or SRAM coupled to the fingerprint pad for storage of one or more fingerprints. According to an embodiment of the invention, the electronic fingerprint pads may have electrically charged surface elements, wherein portions of the surface are electrically discharged upon contact with the finger surface, such as the ridges of the finger surface, such that the fingerprint is recorded in the pattern of discharged elements, whereby the fingerprint pattern may be stably stored within the surface for a time after it is created until it is read, for example through connection of the apparatus with an external device, including without limitation a base station. An embodiment of the invention include means of transmission of the captured fingerprint, for example to an external device or network, including without limitation through a hard-wired connection, for example employing wires, cables, or a docking station or docking connector, for employing a connection including without limitation USB, IEEE 1394, serial, parallel, or SCSI, or a wireless connection, for example employing infrared, RF, IEEE 802.11, Bluetooth, IEEE 802.15, or Wi-Fi.

In an embodiment of the invention, a cover encloses the fingerprint acquisition pad. The cover may be secured using various mechanisms, for example, without limitation, a tab-and-slot connector, latch, spring latch, adhesive tape, or security tape. The cover may be secured prior to fingerprint acquisition and/or after fingerprint acquisition.

FIGS. 1-5 depict a fluid collection and analyte testing device in accordance with an embodiment of the present invention. Analyte screening device 10 includes a fluid collector 20, to collect a fluid sample from a test subject, and a housing 30 to test and retain the fluid sample. The housing 30 contains a collection chamber 40, to receive the fluid collector 20 through an opening 32, at least one membrane test strip 51, to indicate the presence or absence of at least one analyte, and an immunoassay-based fingerprint acquisition pad 60 to positively identify an individual associated with the test. The collection chamber 40 is in fluid communication, with the membrane test strips 51 and the immunoassay-based fingerprint acquisition pad 60.

Referring still to FIGS. 1-5, the fluid collector 20 receives a fluid sample from a test subject and temporarily stores the fluid sample until it is transferred to the housing 30. Generally, any material capable of acquiring and storing a fluid sample may be used. A sponge 25 is attached to one end of the fluid collector 20 to absorb, and temporarily store, the fluid sample. The sponge 25 may be saturated with a saliva-producing substance. After the fluid sample has been collected, the fluid collector 20 is inserted into the collection chamber 40 through the opening 32, and the fluid sample is expelled by compressing the sponge 25 against the bottom surface of the lower portion 42 of the collection chamber 40, thereby releasing the entrapped fluid into the apparatus.

Referring still to FIGS. 1-5, the fluid collector 20 includes a central shaft 22, a disk 21, disposed at the upper end of the central shaft 22, a disk 24, disposed at the lower end of central shaft 22, and a handle 23 attached to the upper surface of the disk 21. The diameter of disk 21 is slightly larger than the diameter of disk 24. Additionally, sealing rings 28 and 29 may be attached to the outer circumference of disks 21 and 24, respectively. Generally, the dimensions of disks 21 and 24, and sealing rings 28 and 29, comport with the interior dimension of collection chamber 40 in order to prevent fluid from escaping through the opening 32. Sponge 25 is attached to the lower surface of disk 24 and is dimensioned to be slightly smaller in diameter than disk 24 to allow for radial expansion within the lower portion 42 of the collection chamber 40 when the sponge 25 is under compression.

Referring still to FIGS. 1-5, as is discussed in more detail below, the fluid collector 20 becomes secured within the collection chamber 40 after the fluid collector 20 is inserted into the collection chamber 40 to a predetermined depth. If desired, handle 23a may then be broken away from the upper surface of disk 21. The analyte screening device 10 also includes a window 36 through which the secured fluid collector 20 may be viewed. The cover 37 encloses immunoassay-based fingerprint acquisition pad 60, and is attached to the housing 30 by the hinges 38. The cover 37 may be secured after the fingerprint of the test subject has been acquired, using various locking mechanisms, including without limitation a tab-and-slot arrangement, or security tape Further confirmation testing may be performed, using the secured fluid sample. Access to the fluid sample may be obtained, for example, by simply removing the immunoassay-based fingerprint acquisition pad 60 to expose adapter 61 and tube 46, by puncturing the immunoassay-based fingerprint acquisition pad 60 with a needle to access adapter 61 and tube 46.

Referring still to FIGS. 1-5, the test cartridge 50, containing the membrane test strips 51, may be inserted into a test cartridge chamber 34 through an opening 33. Advantageously, different versions of the test cartridge 50 may be developed to test different combinations of analytes, thereby allowing the test administrator to select the appropriate analyte test suite at the test site. The test cartridge chamber 34 includes a locking mechanism 35 to secure the test cartridge 50 within the test cartridge chamber 34, thereby preventing the removal of the test cartridge 50 from housing 30. The locking mechanism 35 cooperates with corresponding structure located on the test cartridge 50. An opening or window 31 in the housing 30 allows a portion of the test cartridge 50 to be viewed, including, of course, the test and control regions of the membrane test strips 51.

Referring still to FIGS. 1-5, each membrane test strip 51 generally indicates the presence or absence of at least one analyte. A single drug, or class of drugs, is indicated by each membrane test strip 51, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol.

Referring still to FIGS. 1-5, immunoassay-based fingerprint acquisition pad 60 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

Referring still to FIGS. 1-5, immunoassay-based fingerprint acquisition pad 60 is fluidicly coupled to the collection chamber 40. A signal-producing agent, located on upper surface of the porous support or the lower surface of the reaction medium, mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample/signal-producing agent mixture permeates the reaction medium, and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Referring still to FIGS. 1-5, a piping system fluidicly couples the collection chamber 40 to the membrane test strips 51 and the immunoassay-based fingerprint acquisition pad 60. Tube 43 fluidicly couples the lower portion 42 of the collection chamber 40 to adapter 44 and test cartridge fluid reservoir 45. Similarly, tube 46 fluidicly couples the lower portion 42 of collection chamber 40 to adapter 61, located just beneath immunoassay-based fingerprint acquisition pad 60. Although tubes 43 and 46 are shown to be individually connected to the lower portion 42 of collection chamber 40, other configurations are also possible. For example, tube 43 may be the only connection to the lower portion 42 of collection chamber 40. In this example, a "T" connection may be incorporated into tube 43 to fluidicly couple tube 46 to immunoassay-based fingerprint acquisition pad 60. Alternatively, the required fluid connections may be molded directly within the housing 30.

Figure 6:
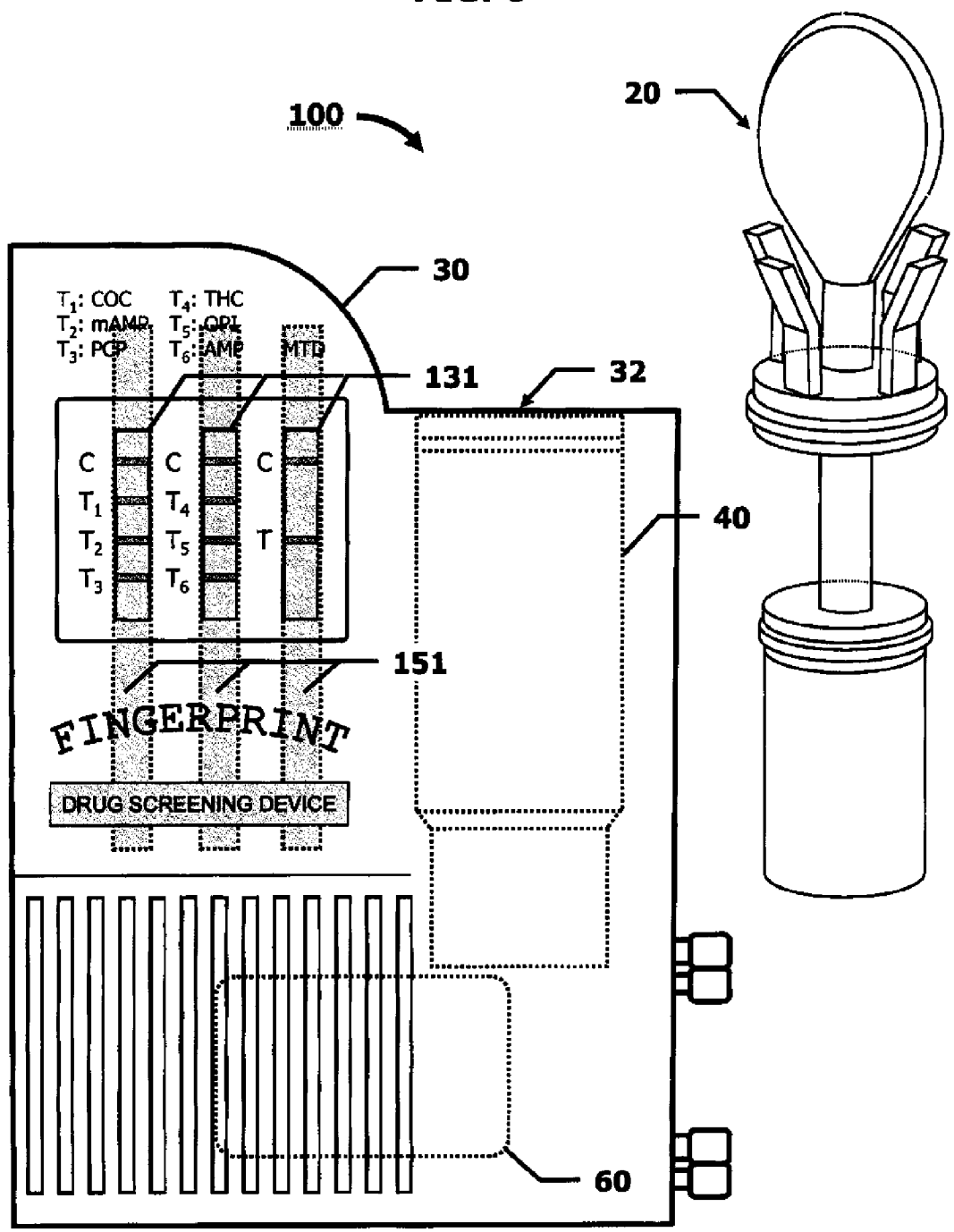
FIG. 6 depicts a front view of a fluid collection and analyte testing device in accordance with an embodiment of the present invention.
Figure 7:
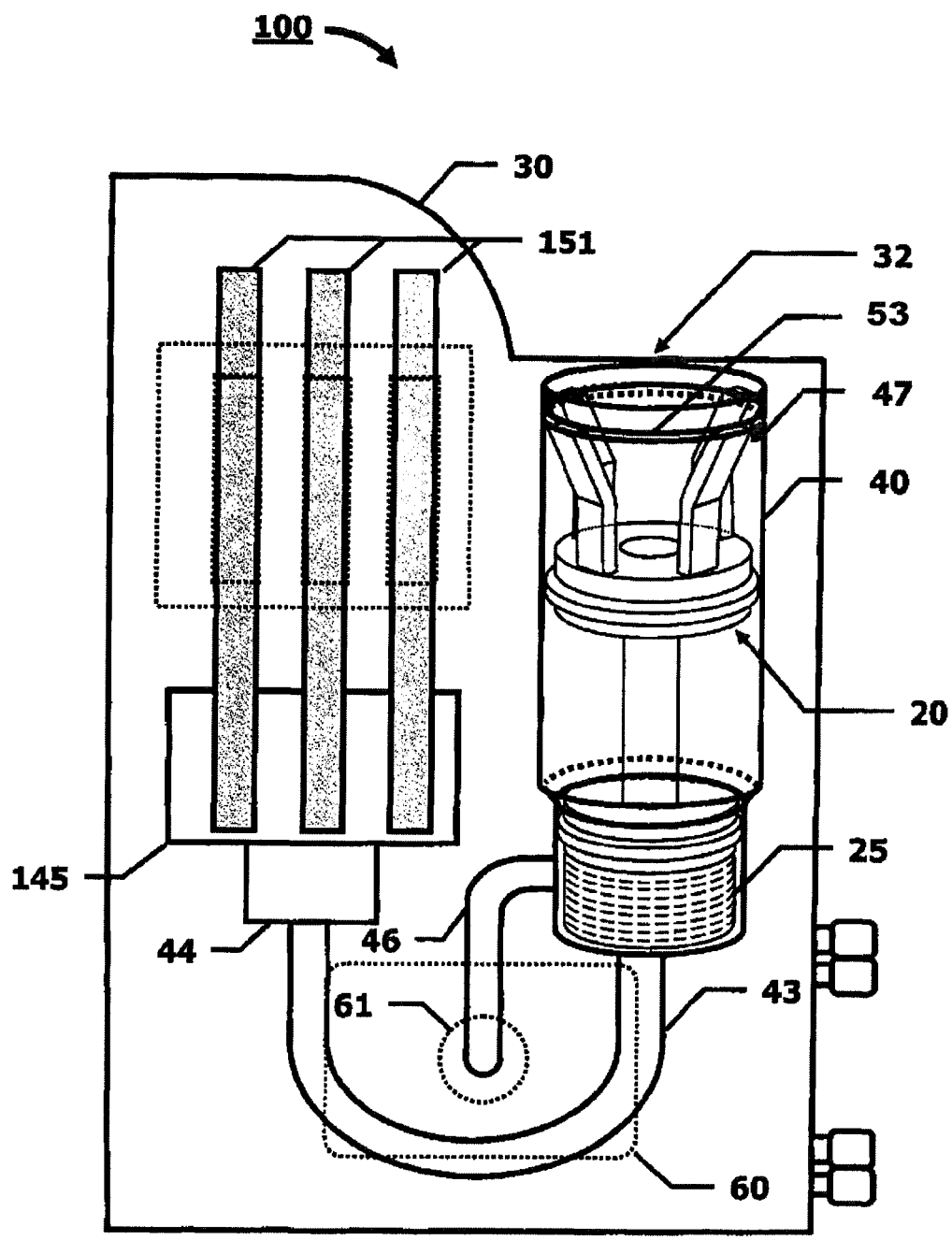
FIG. 7 depicts a front cutaway view of a fluid collection and analyte testing device in accordance with an embodiment of the present invention.
Figure 8:
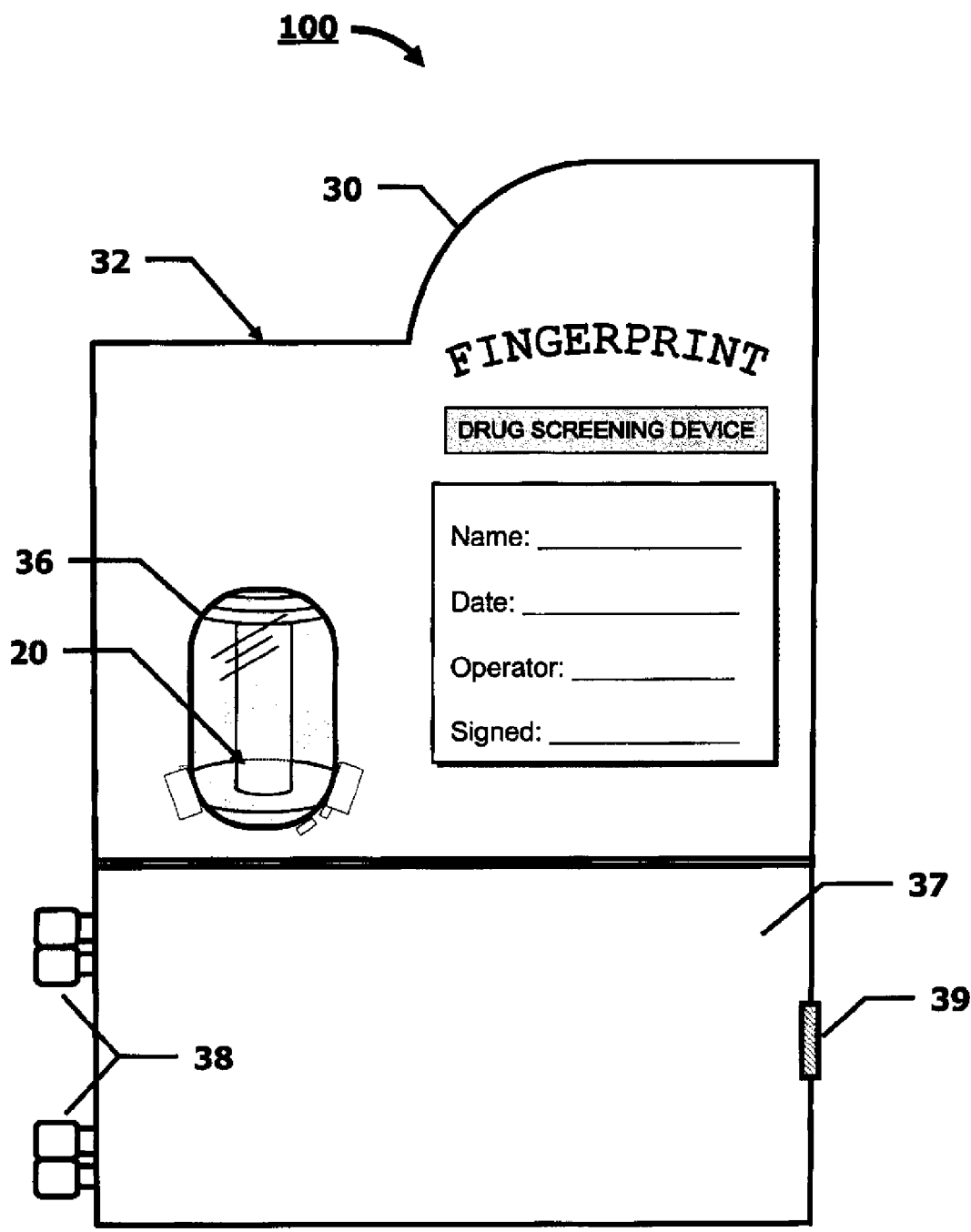
FIG. 8 depicts a back view of a fluid collection and analyte testing device in accordance with an embodiment of the present invention.

FIGS. 6-8 depict a fluid collection and analyte testing device in accordance with an embodiment of the present invention. Analyte screening device 100 includes membrane test strips 151 attached directly to housing 30. The membrane test strips are coupled to a fluid reservoir 145. Several analytes are indicated by each membrane test strip 151, including without limitation, for example, cocaine (COC), methamphetamine (mAMP) and phencyclidine (PCP) (leftmost strip), marijuana (THC), opiates and amphetamine (AMP) (middle strip) and methadone (MTD) (rightmost strip). In additional to recognized standards, minimum concentration levels at which a positive reaction is produced, that is, no visible line in the test region of the membrane test strip, may include, for example, amphetamine (50 ng/mL), methamphetamine (50 g/mL), a cocaine metabolite including benzoylecgnonine and ecgonine methyl ester (20 ng/mL), an opiate including morphine, codeine and heroine (40 ng/mL), marijuana (THC COOH) (12 ng/mL) and phencyclidine (10 ng/mL). Several openings or windows 131 in the housing 30 allow the test and control regions of the membrane test strips 151 to be viewed.

Referring still to FIGS. 6-8, the fluid collector 20 receives a fluid sample from a test subject and temporarily stores the fluid sample until it is transferred to the housing 30. The fluid collector 20 is then inserted into the collection chamber 40 through the opening 32, and the fluid sample is extracted therefrom by compressing the sponge 25 against the bottom surface of the lower portion 42 of the collection chamber 40, thereby releasing the entrapped fluid into the tubes 43 and 46. Projections 26 extend from the upper surface of disk 21 and cooperate with an annular projection 53, located on the inner surface of the collection chamber 40, to secure the fluid collector 20 within the collection chamber 40.

Referring to FIGS. 7-8, after the fluid collector 20 is inserted a predetermined distance, the projections 26 engage the annular projection 53 to prevent the fluid collector 20 from being extracted from the collection chamber 40. Although four projections are depicted, at least two should be used to effectively secure the fluid collector 20 within the collection chamber 40. Alternatively, the annular projection 53 may cooperate with a projecting circumferential ring (not show), located above the sealing ring 28 of disk 21, to secure the fluid collector 20 within the collection chamber 40. As an additional measure of security, handle 23a may be detached from the fluid collector 20 along a line of weakness 27 after the fluid collector 20 has engaged the annular projection 53. If a twisting motion is desired to detach the handle 23 from the fluid collector 20, then one (or more) stop(s) 47 may be located just below the annular projection 53 to prevent the fluid collector 20 from rotating by engaging one (or more) of the projections 26.

Figure 9:
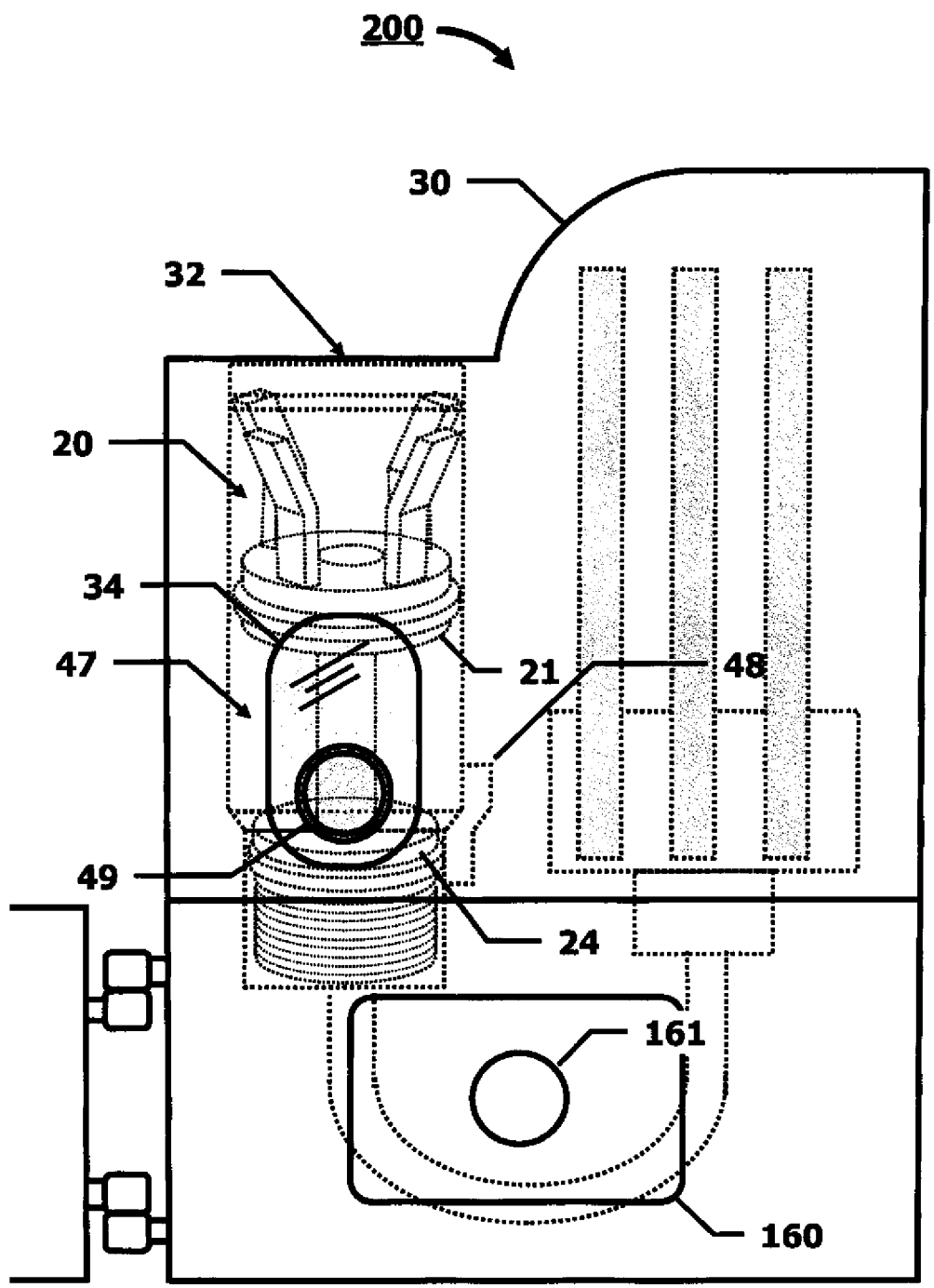
FIG. 9 depicts a back view of a fluid collection and analyte testing device in accordance with an embodiment of the present invention.

Referring to FIG. 9, analyte screening device 200 includes a window 37 incorporating a sealable opening 49 that allows access to the collection chamber 40. When the fluid collector 20 is secured within the collection chamber 40, sealable opening 49 allows access to a confirmation chamber 47 formed between the disks 21 and 24. A passage 48 fluidicly couples the lower portion 42 of the collection chamber 40 to the confirmation chamber 47 to allow a portion of the fluid sample to flow into the confirmation chamber 47 as the fluid collector 20 is inserted into the collection chamber 40. Once the fluid collector 20 is secured with the collection chamber 40, a portion of the fluid sample is available for confirmation sampling through the sealable opening 49.

Referring still to FIG. 9, immunoassay-based fingerprint acquisition pad 60 is not fluidicly coupled to the collection chamber 40. Instead, a portion of the fluid sample is extracted through the sealable opening 49, using, for example, a pipette, and applied to the upper surface of immunoassay-based fingerprint acquisition pad 60. A signal-producing agent is applied to the person's fingertip, or, alternatively, the signal-producing agent may be located on the upper surface of the porous support or the lower surface of the reaction medium. The signal-producing agent then mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample permeates the reaction medium, and allowing the predetermined ligand/receptor reaction to take place so that the members of the immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Figure 10:
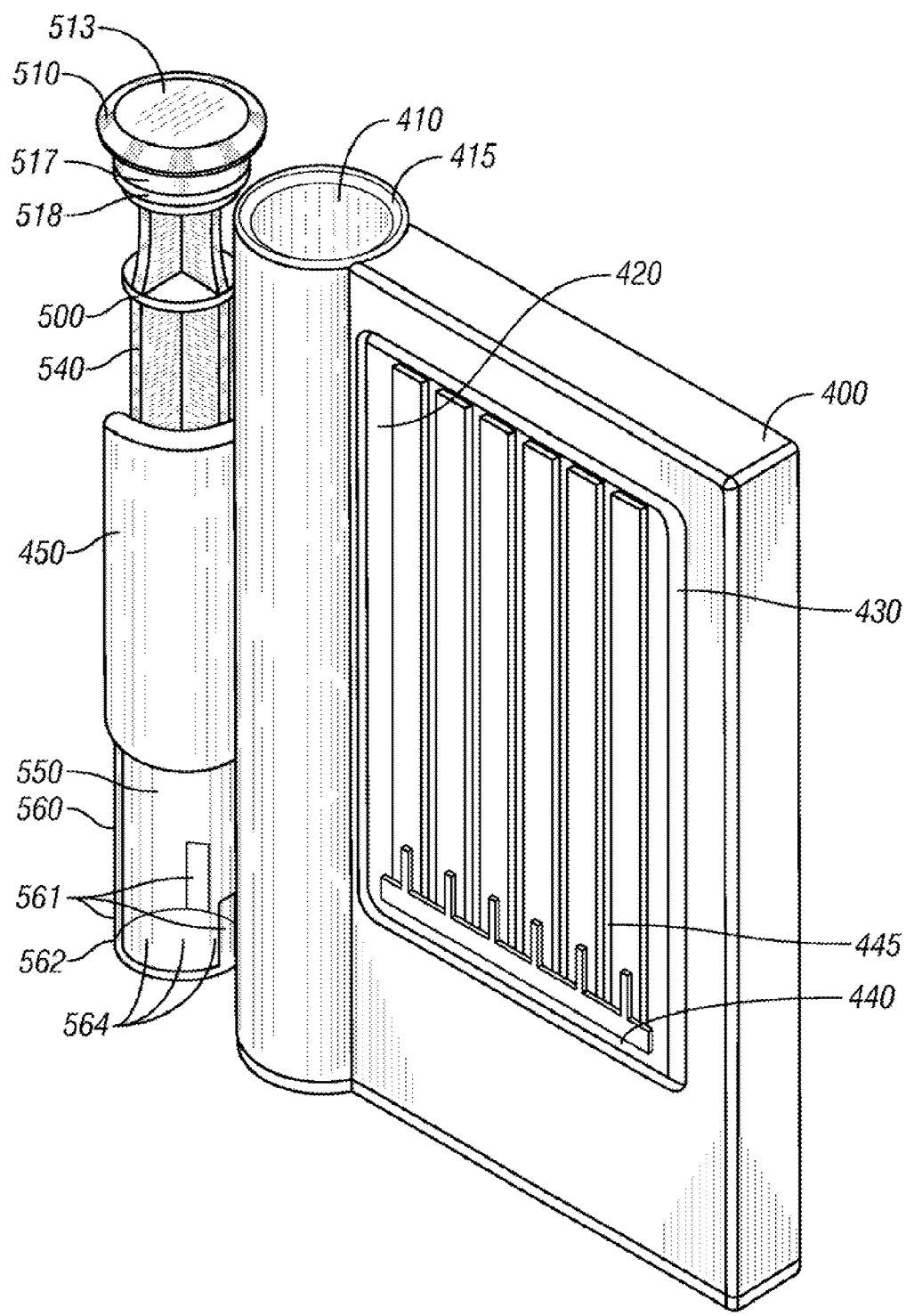
FIG. 10 depicts an isometric view of a fluid collection and analyte testing device in accordance with an embodiment of the present invention, in which a fluid collector rests in its holder in an analyte testing device.

Referring to FIG. 10, a fluid collector 500 rests in a fluid collector holder 450 attached to analyte testing device 400. The fluid collector 500 includes an upper segment 510 having an upper surface 513, a closure member 517, and a sealing member 518; a shaft 540; a housing 560 having several lateral openings 561, lower openings 564, and lower surface 562 and containing absorbent material 550. The analyte testing device 400 includes a receiving member 410 having an open end 415; a membrane test strip 420; a window 430 for viewing of the membrane test strip; a lower fluid channel 440; and an upper fluid channel 445.

Figure 11:
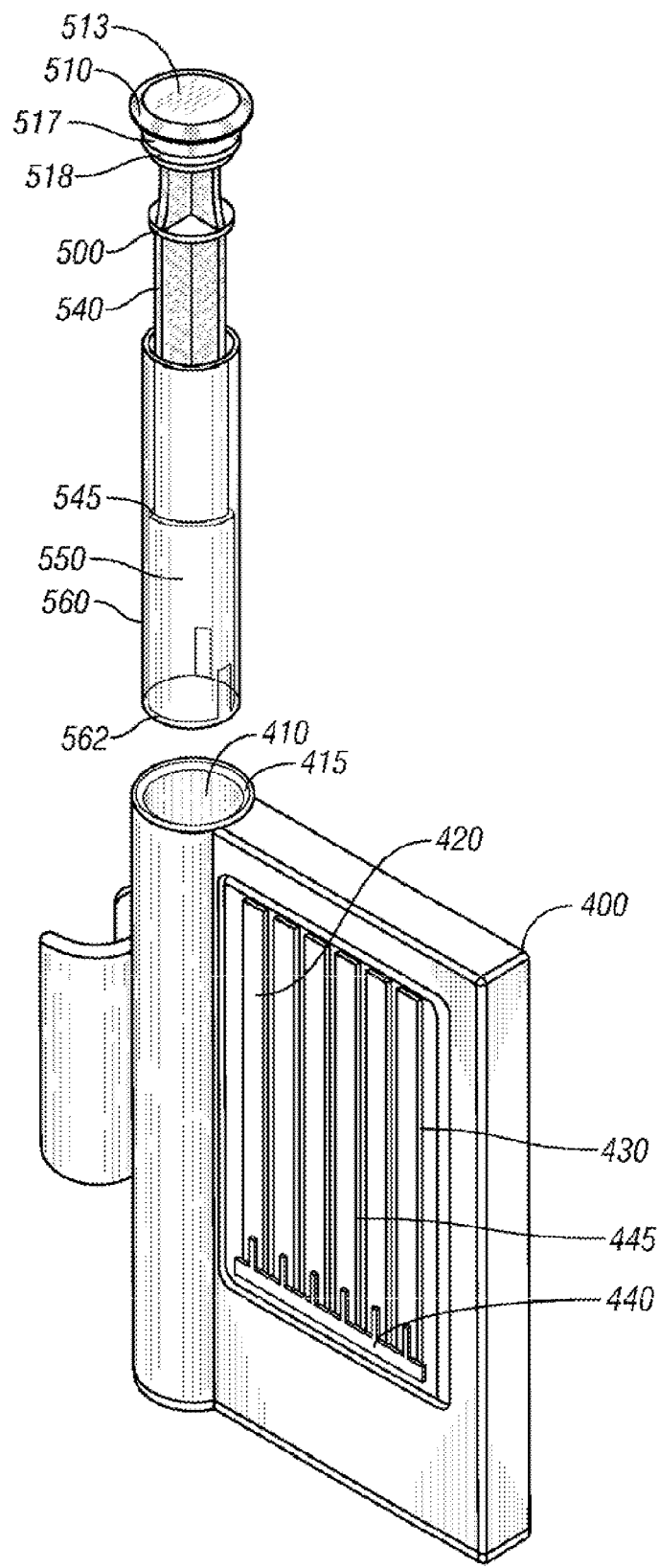
FIG. 11 depicts an isometric view of a fluid collection and analyte testing device in accordance with an embodiment of the present invention, in which a fluid collector is being inserted into an analyte testing device.

Referring to FIG. 11, after a fluid sample has been absorbed by absorbent material 550 the fluid collector 500 is inserted into the open end 415 of the receiving member 410.

Figure 12:
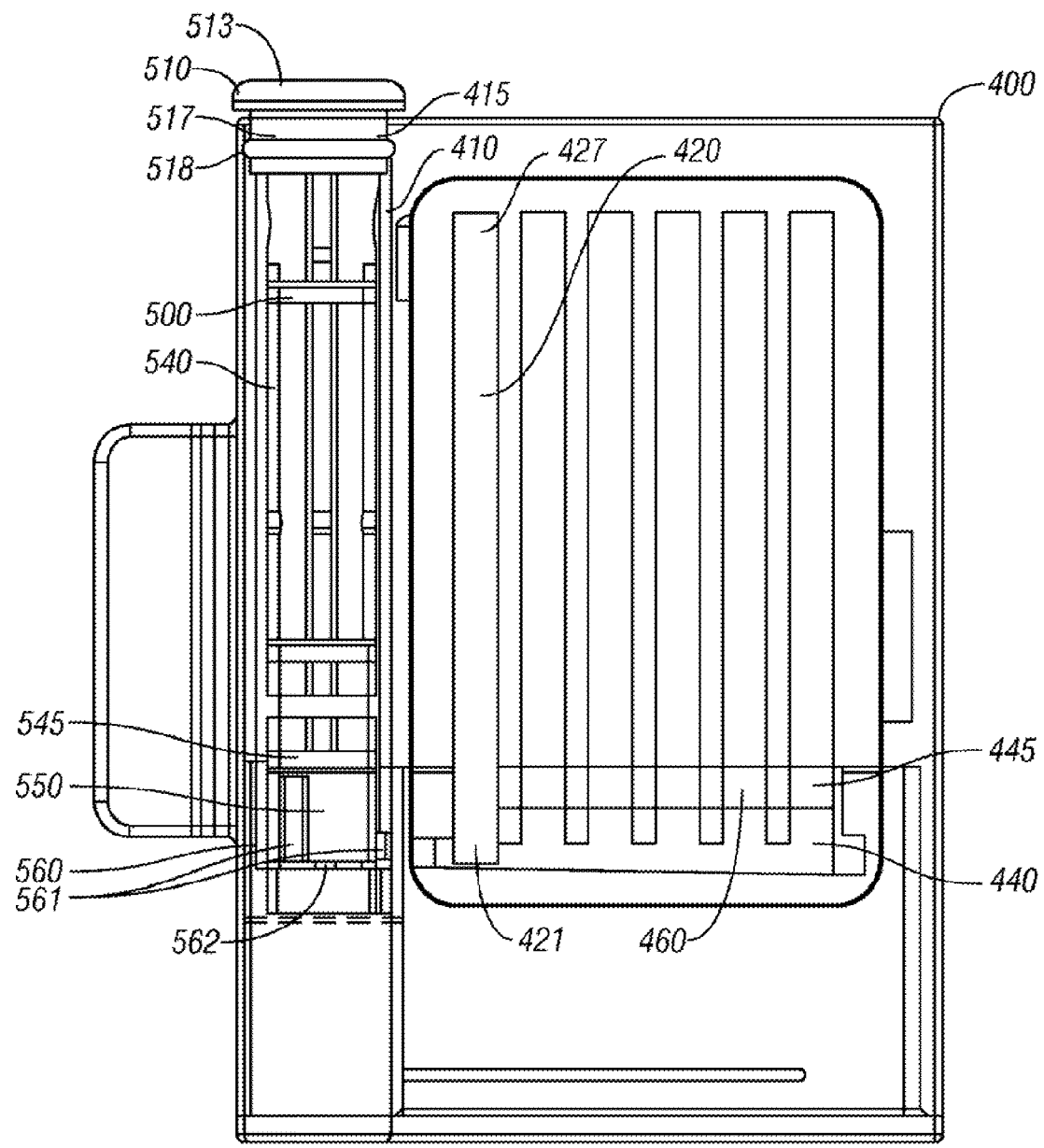
FIG. 12 depicts a front cross-sectional view of a fluid collection and analyte testing device in accordance with an embodiment of the present invention.

Referring to FIG. 12, compression of the upper surface 513 of the fluid collector 500 has caused closure element 517 to seat in the open end 415 of the receiving member 410, where sealing member 518 forms a seal. The fluid collector 500 has been fully inserted into the testing device 400, and the absorbent material 550 has been compressed between the compression element 545 and the lower surface 562 of the housing 560, causing the fluid sample to be expelled through openings 561. The fluid sample flows through lower channel 440 and encounters the proximal end 421 of the membrane test strip 420 and begins to upward towards the upper end 427 of the membrane test strip 420 by capillary action. Once a sufficient volume of the fluid sample has entered the lower channel 440, the fluid level rises until excess fluid flows through upper channel 445 and enters an absorbent pad, sample retention member 460.

Figure 13:
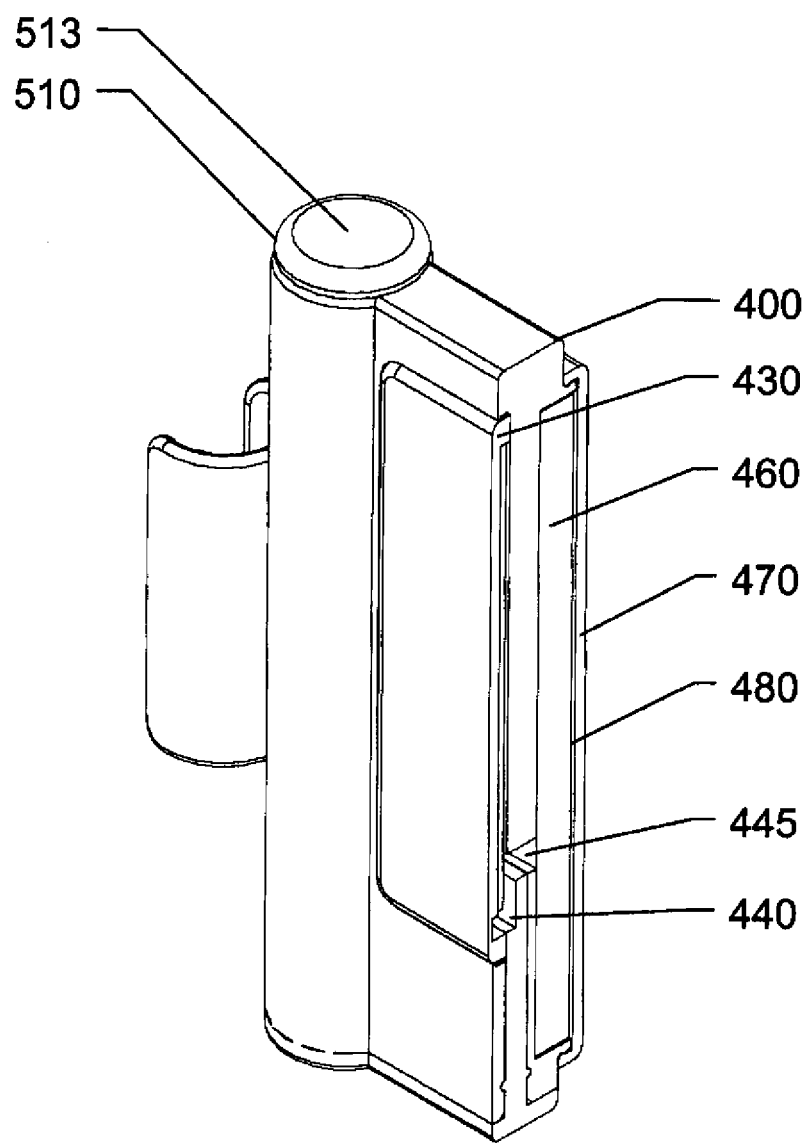
FIG. 13 depicts an isometric cross-sectional view of a fluid collection and analyte testing device in accordance with an embodiment of the present invention.

Referring to FIG. 13, the fluid sample fills the lower channel 440 before flowing into the upper channel 445 to enter the sample retention member 460. The sample retention member 460 is bonded to fingerprint acquisition pad 480, which is covered by the rear door 470.

Figure 14:
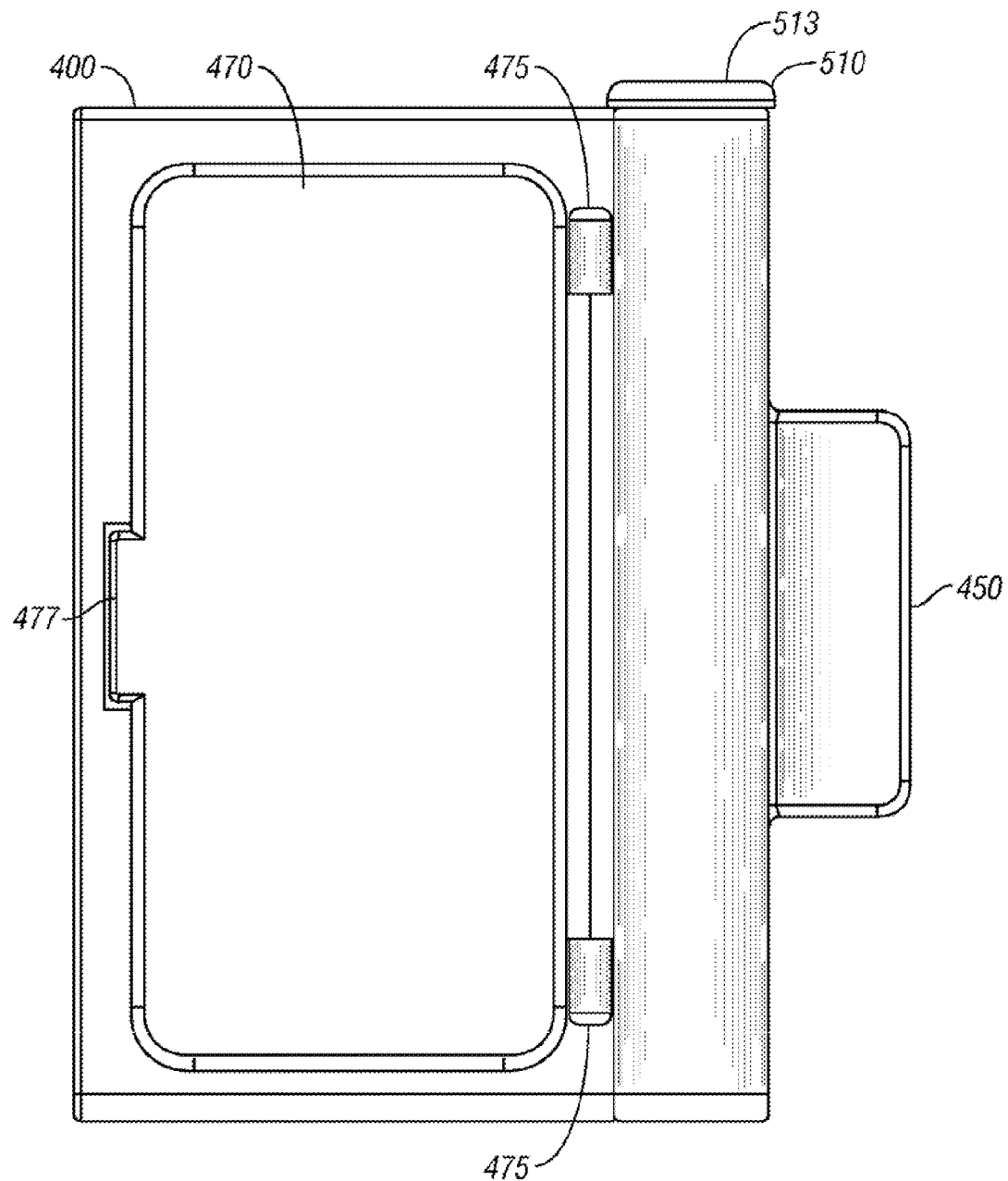
FIG. 14 depicts a rear view of a fluid collection and analyte testing device in accordance with an embodiment of the present invention.

Referring to FIG. 14, the fingerprint acquisition pad is covered by the rear door 470 which is held closed by closure member 477 and pivots into the opened position on the axis defined by the hinges 475.

Figure 15:
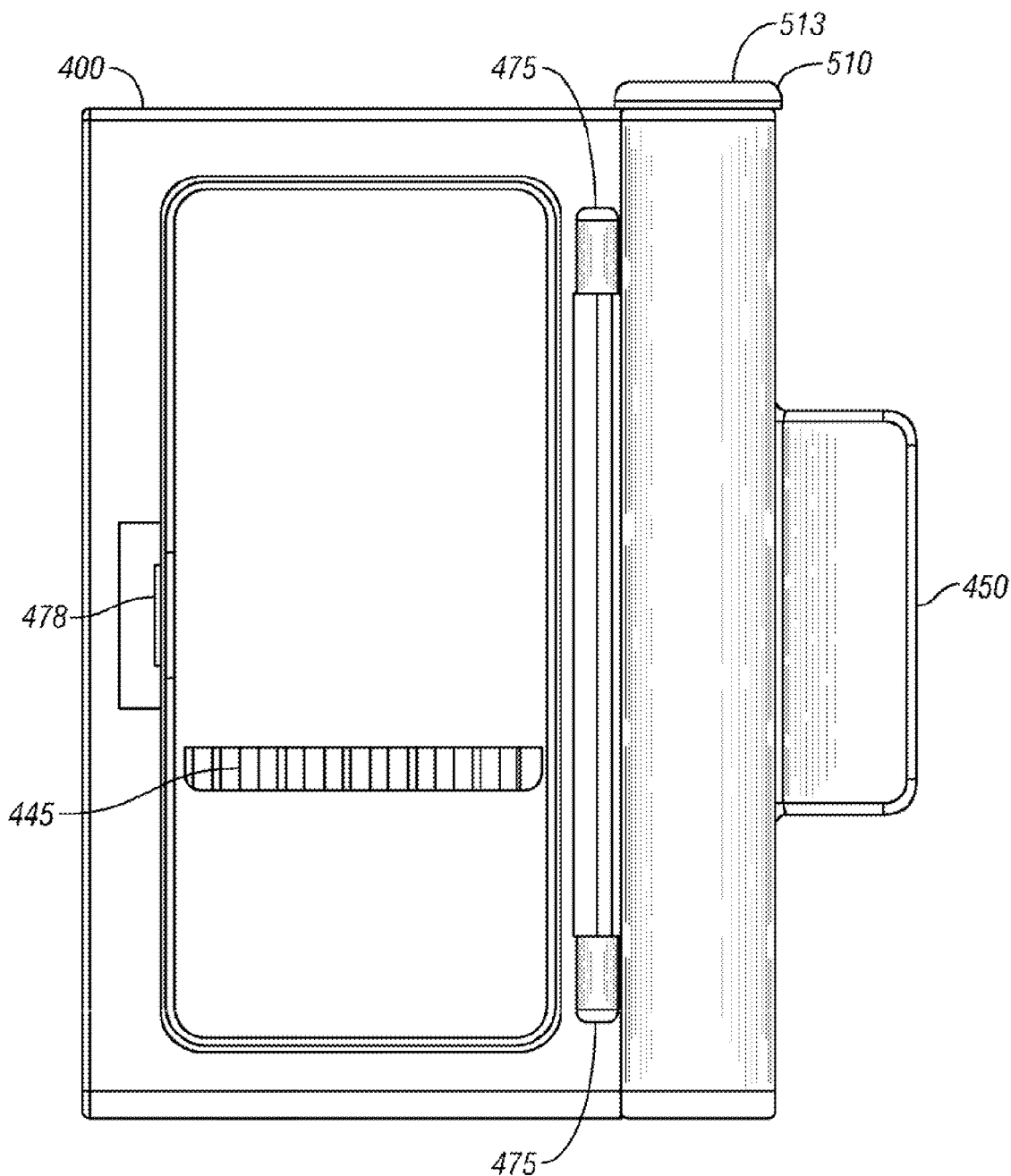
FIG. 15 depicts a rear view of a fluid collection and analyte testing device in accordance with an embodiment of the present invention having the rear door and fingerprint removed to show a fluid channel beneath.

Referring to FIG. 15, the rear door, fingerprint acquisition pad, and sample retention member are hidden to show a rear view of the upper channel 445 through which the fluid sample flows to enter the sample retention member. The closure member of the rear door cooperates with latch member 478 to secure the door in the closed position.

Figure 16:
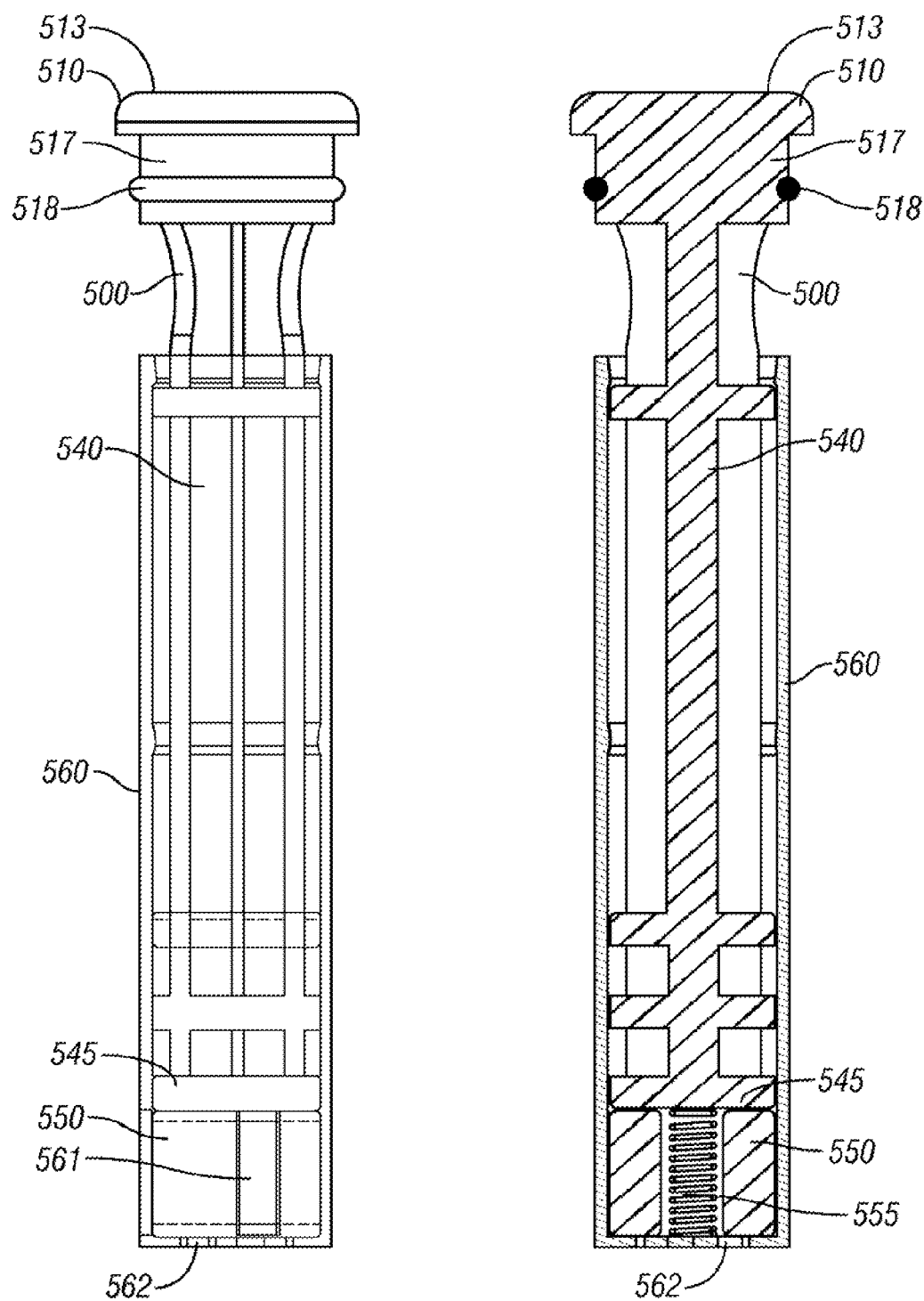
FIG. 16 depicts a front view and a cross-sectional front view of a fluid collection device in accordance with an embodiment of the present invention.

Referring to FIG. 16, the left and right panels show exterior and cross-sectional views, respectively, of a fluid collector 500. The fluid collector 500 includes a spring 555 that is co-axial with the direction of compression of absorbent material 550, such that compression of the absorbent material 550 results in compression of the spring 555, and release of the compressive force causes the spring 555 to assist the return of the absorbent material 550 to the relaxed state, creating suction that draws the fluid sample into the absorbent material 550.

Figure 17:
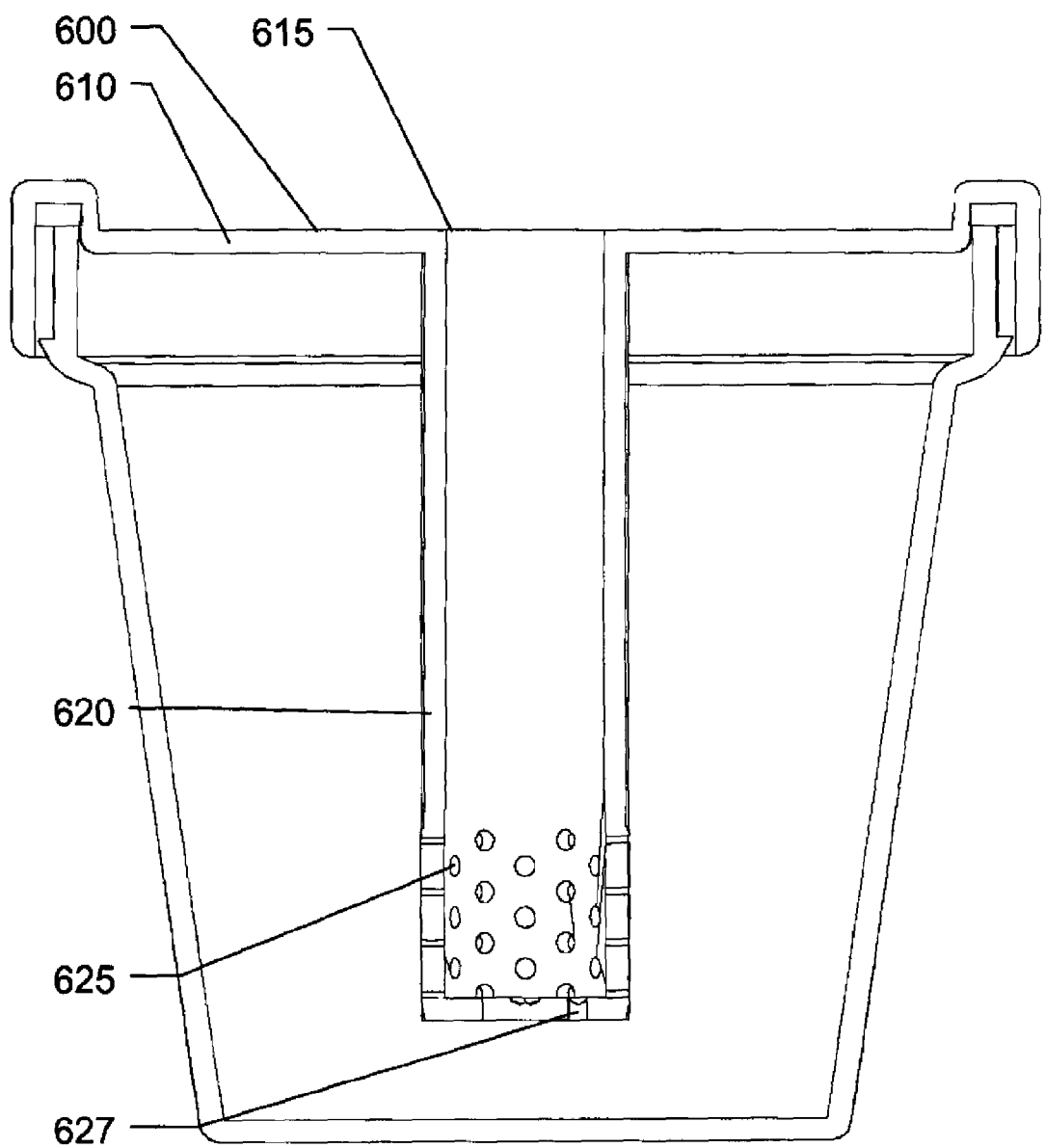
FIG. 17 depicts a cross-sectional front view of a urine cup in accordance with an embodiment of the present invention.

Referring to FIG. 17, a urine cup 600 able to receive a fluid collector has a lid 610 having an opening 615 leading to the interior of supporting member 620 having openings 625 through which the fluid sample can flow, and slot 627 that cooperates with the fluid collector.

Figure 18:
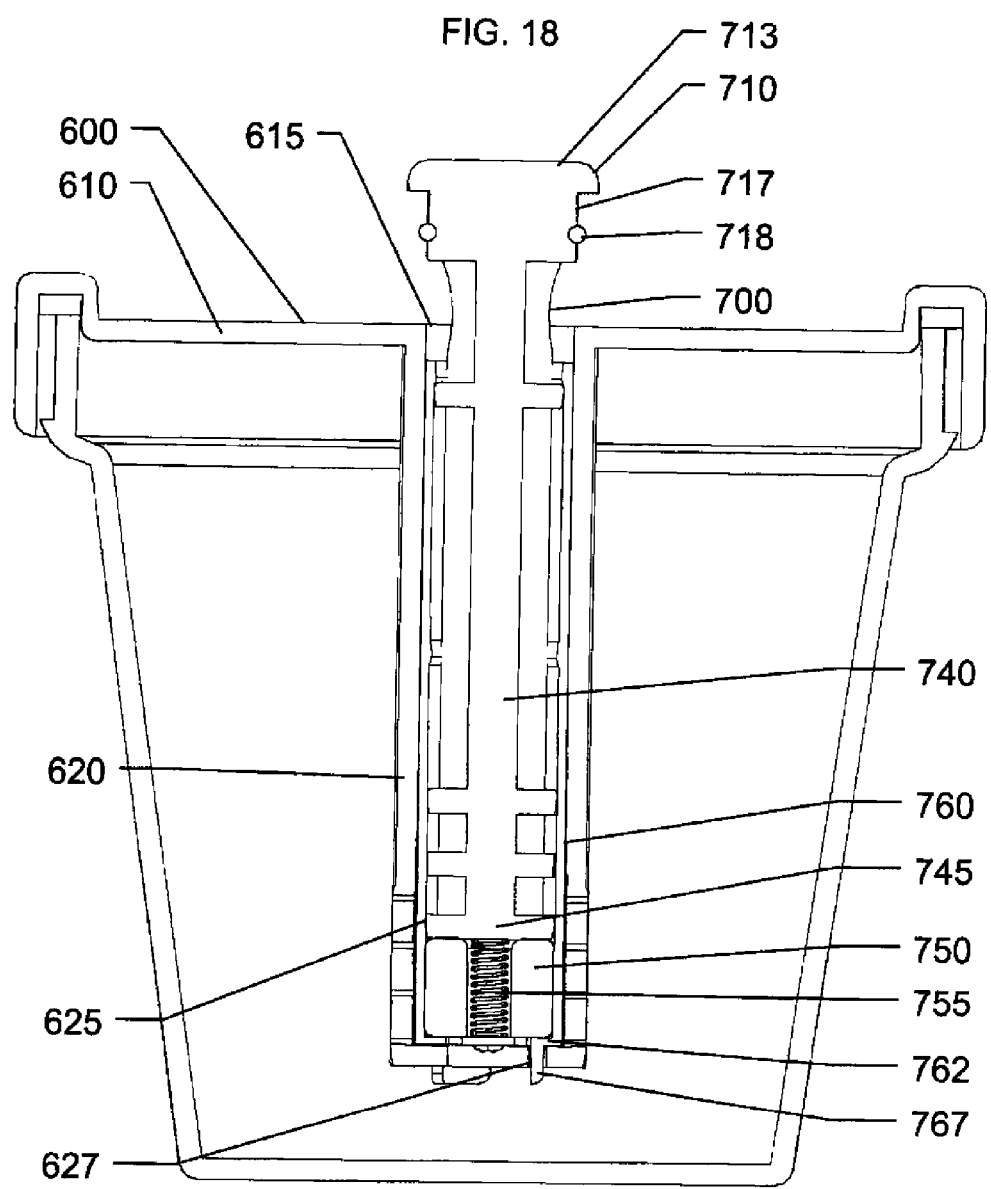
FIG. 18 depicts a cross-sectional front view of a urine cup with a fluid collector inserted therein in accordance with an embodiment of the present invention.

Referring to FIG. 18, a fluid sample collector 700 has been inserted through the opening 615 into the interior of the supporting member 620, and a tab 762 disposed on the lower end of the fluid sample collector has engaged slot 627, whereby housing 760 is prevented from rotating relative to the urine collection cup 600. The absorbent material 750 is compressed between the compression member 745 and the lower surface 762 of the housing. When the compressive force is released, a spring 755 co-axial with absorbent material 750 assists the return of absorbent material 750 to the relaxed state, creating suction that helps draw the fluid sample into the absorbent material 750. The sample collection 700 apparatus also includes upper segment 710 having an upper surface 713 through which compressive force is delivered to the absorbent material 750, a closure member 717, a sealing member 718, and a shaft 740.

Although this invention has been described in conjunction with specific embodiments thereof, many alternatives, modifications and variations will be apparent to those skilled in the art. Accordingly, the preferred embodiments of the invention as set forth herein, are intended to be illustrative, not limiting. Various changes may be made without departing from the true spirit and full scope of the invention as set forth herein.

What is claimed is:

1. An apparatus comprising:
   a sample receiving member having an opening for receiving a fluid sample;
   a sample retention member in fluid communication with the sample receiving member to retain a portion of the fluid sample;
   at least one membrane test strip in fluid communication with the sample receiving member to indicate the presence or absence of at least one analyte in the fluid sample; and
   a fluid collector to collect the fluid sample and convey the fluid sample into the sample receiving member,
      wherein the fluid collector comprises an absorbent material to absorb the fluid sample; a compression member operatively associated with the absorbent material; and a closure member capable of sealing the open end of the sample receiving member when the fluid collector is inserted in the sample receiving member.

2. The apparatus of claim 1, wherein the closure member is capable of creating an airtight seal in the open end of the sample receiving member.

3. The apparatus of claim 1, further comprising means for securing the fluid collector within the sample receiving member after the fluid collector has been inserted into the sample receiving member.

4. The apparatus of claim 3, wherein the means for securing the fluid collector within the sample receiving member comprise at least one annular projection within the sample receiving member.

5. The apparatus of claim 1, wherein the fluid collector further comprises a handle removably attached to the upper surface of the closure member.

6. The apparatus of claim 1, further comprising a saliva-producing substance.

7. The apparatus of claim 6, wherein the saliva-producing substance is sugar, salt, acid, or any combination thereof.

8. The apparatus of claim 7, wherein the saliva-producing substance is sodium chloride, citric acid, or any combination thereof.

9. The apparatus of claim 1, further comprising a fingerprint acquisition pad.

10. The apparatus of claim 9, wherein the fingerprint acquisition pad is enclosed by a cover attached to the housing.

11. The apparatus of claim 9, wherein the fingerprint acquisition pad is an ink-based fingerprint acquisition pad.

12. The apparatus of claim 11, further comprising a dispenser able to dispense an ink that can elicit a signal in the ink-based fingerprint acquisition pad.

13. The apparatus of claim 9, wherein the fingerprint acquisition pad is an inkless fingerprint acquisition pad.

14. The apparatus of claim 13, further comprising a dispenser able to dispense an activator that can elicit a signal in the inkless fingerprint acquisition pad.

15. The apparatus of claim 13, wherein the inkless fingerprint acquisition pad is an immunoassay-based fingerprint acquisition pad.

16. The apparatus of claim 15, wherein the immunoassay-based fingerprint acquisition pad is in fluid communication with the sample receiving member.

17. The apparatus of claim 16, wherein a channel provides the fluid communication between the sample receiving member and the at least one membrane test strip and the fluid communication between the sample receiving member and the immunoassay-based fingerprint acquisition pad.

18. The apparatus of claim 17, further comprising a dispenser able to dispense a signal-producing agent that can elicit a signal in the immunoassay-based fingerprint acquisition pad.

19. An apparatus for testing a fluid sample comprising at least one test strip in combination with a sample receiving member having an open end and a fluid collector, the fluid collector including:
- an absorbent material, to absorb a fluid sample;
- a compression member operatively associated with the absorbent material,
  - wherein the compression member is configured for selective compression of the absorbent material against a surface of the sample receiving member to cause the absorbent material to expel at least a portion of the fluid sample when the fluid collector is inserted in the sample receiving member; and
- a closure member, capable of sealing the open end of the sample receiving member
- when the fluid collector is inserted into the sample receiving member, wherein the at least one test strip is configured to indicate the presence or absence of at least one analyte in the at least a portion of the fluid sample upon expulsion of the at least a portion of the fluid sample from the absorbent material.

20. The apparatus of claim 1, wherein the compression member is configured for selective compression of the absorbent material against a surface of the sample receiving member to cause the absorbent material to expel at least a portion of the fluid sample when the fluid collector is inserted in the sample receiving member.

* * * * *